(12) United States Patent
Janssen et al.

(10) Patent No.: US 9,731,258 B2
(45) Date of Patent: Aug. 15, 2017

(54) MIXING AND DISPENSING CURABLE MULTI-COMPONENT MATERIALS

(75) Inventors: Jeffrey R. Janssen, Ho Chi Min (VN); Mark F. Schulz, Lake Elmo, MN (US); Scott D. Gullicks, Apple Valley, MN (US); Dennis R. Keicher, River Falls, WI (US); Bruce R. Broyles, Oakdale, MN (US); Ryan Patrick Simmers, Cottage Grove, MN (US); Jameel R. Qiblawi, North Hudson, WI (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 2120 days.

(21) Appl. No.: 11/957,296

(22) Filed: Dec. 14, 2007

(65) Prior Publication Data

US 2008/0144426 A1    Jun. 19, 2008

Related U.S. Application Data

(60) Provisional application No. 60/870,264, filed on Dec. 15, 2006, provisional application No. 60/973,624, filed on Sep. 19, 2007.

(51) Int. Cl.
*B01F 15/02* (2006.01)
*B01F 13/00* (2006.01)
(Continued)

(52) U.S. Cl.
CPC ............ *B01F 15/0441* (2013.01); *A61C 5/64* (2017.02); *B01F 7/00216* (2013.01);
(Continued)

(58) Field of Classification Search
CPC  B01F 7/00216; B01F 13/002; B01F 13/0027; B01F 15/0087; B01F 15/0441;
(Continued)

(56) References Cited

U.S. PATENT DOCUMENTS 2,826,339 A * 3/1958 Maillard ................. 222/137
3,767,085 A 10/1973 Cannon et al.
(Continued)

FOREIGN PATENT DOCUMENTS

DE  2315114  10/1974
DE  3307558  9/1984
(Continued)

OTHER PUBLICATIONS

"Brochure", ConProTec Inc., [available on the internet Dec. 13, 2007], copyright 2000-2007, URL <http://www.conprotec.com/mixpac.php.
(Continued)

*Primary Examiner* — William H Beisner
*Assistant Examiner* — Danielle Henkel
(74) *Attorney, Agent, or Firm* — Aleksander Medved

(57) ABSTRACT

Methods, apparatus, devices and systems for mixing and dispensing multi-component materials. The mixing and dispensing may be performed using a mobile, enclosed dispenser that can be used to supply a mixed multi-component material at the point of use. In some embodiments, the components to be mixed into the multi-component material may be supplied in cartridges.

17 Claims, 21 Drawing Sheets

(51) Int. Cl.
| | | |
|---|---|---|
| *C08F 20/10* | (2006.01) | |
| *B01F 15/04* | (2006.01) | |
| *B01F 7/00* | (2006.01) | |
| *B01F 15/00* | (2006.01) | |
| *B05C 17/005* | (2006.01) | |
| *B05C 17/01* | (2006.01) | |
| *B05C 17/015* | (2006.01) | |
| *B65D 81/32* | (2006.01) | |
| *A61C 5/64* | (2017.01) | |
| *A61C 5/68* | (2017.01) | |

(52) U.S. Cl.
CPC ........ *B01F 7/00291* (2013.01); *B01F 13/002* (2013.01); *B01F 13/0027* (2013.01); *B01F 15/0087* (2013.01); *B05C 17/00553* (2013.01); *B05C 17/00566* (2013.01); *B05C 17/0103* (2013.01); *B05C 17/015* (2013.01); *B65D 81/325* (2013.01); *A61C 5/68* (2017.02); *B01F 2215/0027* (2013.01); *B05C 17/014* (2013.01); *B05C 17/0133* (2013.01)

(58) Field of Classification Search
CPC ......... B01F 7/00291; B01F 2215/0027; B05C 17/00553; B05C 17/00566; B05C 17/0103; B05C 17/015; B05C 17/0133; B05C 17/014; B65D 81/325; A61C 5/64; A61C 5/68
USPC ......... 366/189, 130, 162, 180.1, 162.3, 138, 366/348; 528/271; 141/100
See application file for complete search history.

(56) References Cited

U.S. PATENT DOCUMENTS

| | | | |
|---|---|---|---|
| 4,067,479 A | | 1/1978 | Moline |
| 4,093,188 A | | 6/1978 | Horner |
| 4,801,008 A | | 1/1989 | Rich |
| 4,801,046 A | * | 1/1989 | Miczka ............... 222/95 |
| 5,027,981 A | * | 7/1991 | Magister ............ 222/137 |
| 5,249,862 A | | 10/1993 | Herold et al. |
| 5,332,122 A | | 7/1994 | Herold |
| 5,386,928 A | | 2/1995 | Blette |
| 5,413,253 A | | 5/1995 | Simmen |
| 5,609,271 A | | 3/1997 | Keller et al. |
| 5,865,537 A | | 2/1999 | Streiff et al. |
| 6,129,244 A | | 10/2000 | Hörth |
| 6,302,574 B1 | * | 10/2001 | Chan ................... 366/160.4 |
| 6,311,871 B1 | | 11/2001 | Binder |
| 6,394,643 B1 | * | 5/2002 | Bublewitz et al. ....... 366/172.1 |
| 6,457,609 B1 | | 10/2002 | Keller |
| 6,520,702 B2 | | 2/2003 | Heusser |
| 6,578,738 B1 | | 6/2003 | Keller |
| 6,837,399 B1 | | 1/2005 | Wagner et al. |
| 6,854,621 B2 | | 2/2005 | Keller |
| 6,892,904 B2 | | 5/2005 | Osborn et al. |
| 6,932,243 B2 | | 8/2005 | Keller |
| 7,040,566 B1 | | 5/2006 | Rodrian et al. |
| 7,214,726 B2 | | 5/2007 | Qian |
| 2003/0137898 A1 | | 7/2003 | Wagner et al. |
| 2004/0085854 A1 | | 5/2004 | Pauser et al. |
| 2004/0173558 A1 | | 9/2004 | Chen |
| 2004/0211789 A1 | | 10/2004 | Osborn |
| 2005/0127119 A1 | | 6/2005 | Keller |
| 2005/0232073 A1 | | 10/2005 | Wagner |
| 2006/0054636 A1 | | 3/2006 | Brennan et al. |
| 2006/0151531 A1 | | 7/2006 | Tikusis |
| 2006/0175434 A1 | | 8/2006 | Escoto, Jr. et al. |
| 2006/0266769 A1 | | 11/2006 | Jackson |
| 2009/0140007 A1 | | 6/2009 | Voss |

FOREIGN PATENT DOCUMENTS

| | | |
|---|---|---|
| DE | 4235736 | 3/1994 |
| EP | 0276665 | 8/1988 |
| EP | 0313519 | 4/1989 |
| EP | 0 319 203 | 6/1989 |
| EP | 0472448 | 2/1992 |
| EP | 0693437 | 1/1996 |
| EP | 1004353 | 1/2003 |
| JP | 64-085120 | 3/1989 |
| JP | 04-290576 | 10/1992 |
| JP | 07-163925 | 6/1995 |
| JP | 7-163925 | 6/1995 |
| JP | 11-105986 | 4/1999 |
| JP | 2000-297018 | 10/2000 |
| JP | 2001-513059 | 8/2001 |
| JP | 2004-155484 | 6/2004 |
| WO | WO 99/43726 | 9/1999 |
| WO | WO 01/00521 | 1/2001 |
| WO | WO 2005/095225 A1 | 10/2005 |
| WO | WO 2006/019299 | 2/2006 |
| WO | WO 2007041878 | 4/2007 |

OTHER PUBLICATIONS

Supplementary European Search Report, Apr. 7, 2010.
Versuchsergenbnisse zur Viskositätsbestimmung, 2012.
Brookfield Digital Rheometer Model DV-III Operating Instructions Manual No. M/91-210-I297.
Technisches Merkblatt zu SikaForce®-7750 L100 (version Oct. 2002).
Technisches Merkblatt zu SikaForce®-7101 L35 (version Oct. 2005).
Produkt Datenblatt zu SikaForce®-7720 L105 (version May 2011).
Technical Data Sheet von SikaForce®-5215 (version Oct. 2003).
Produkt Datenblatt von SikaFlex®-254 Booster (version Sep. 2006).

* cited by examiner

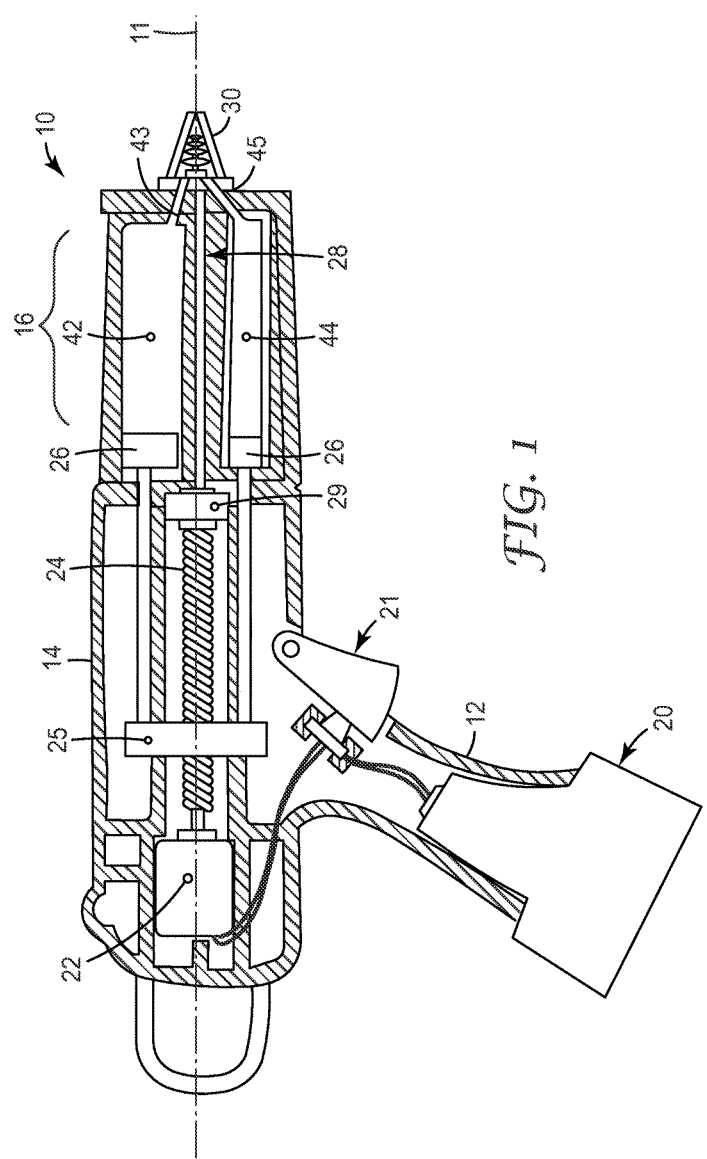

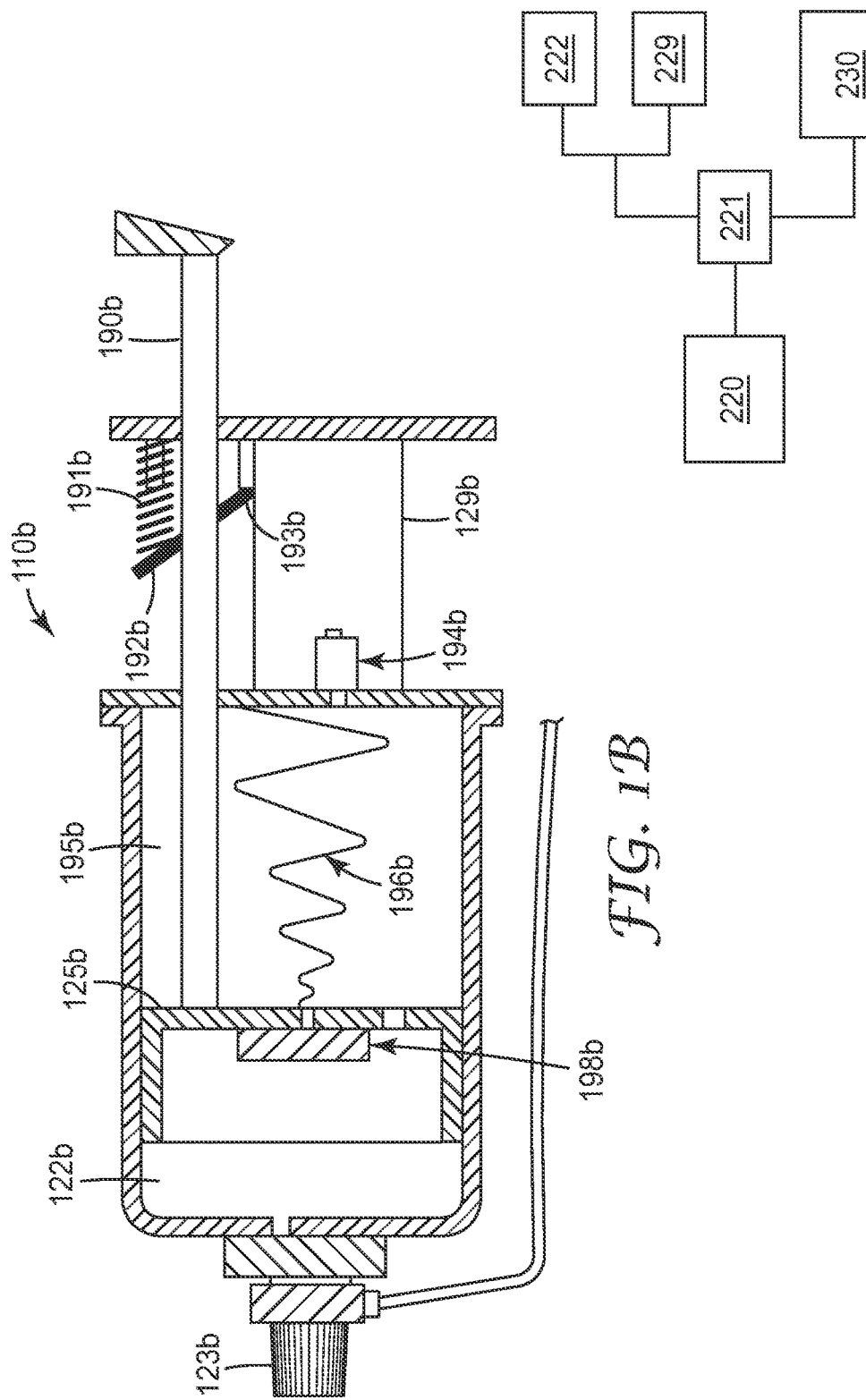

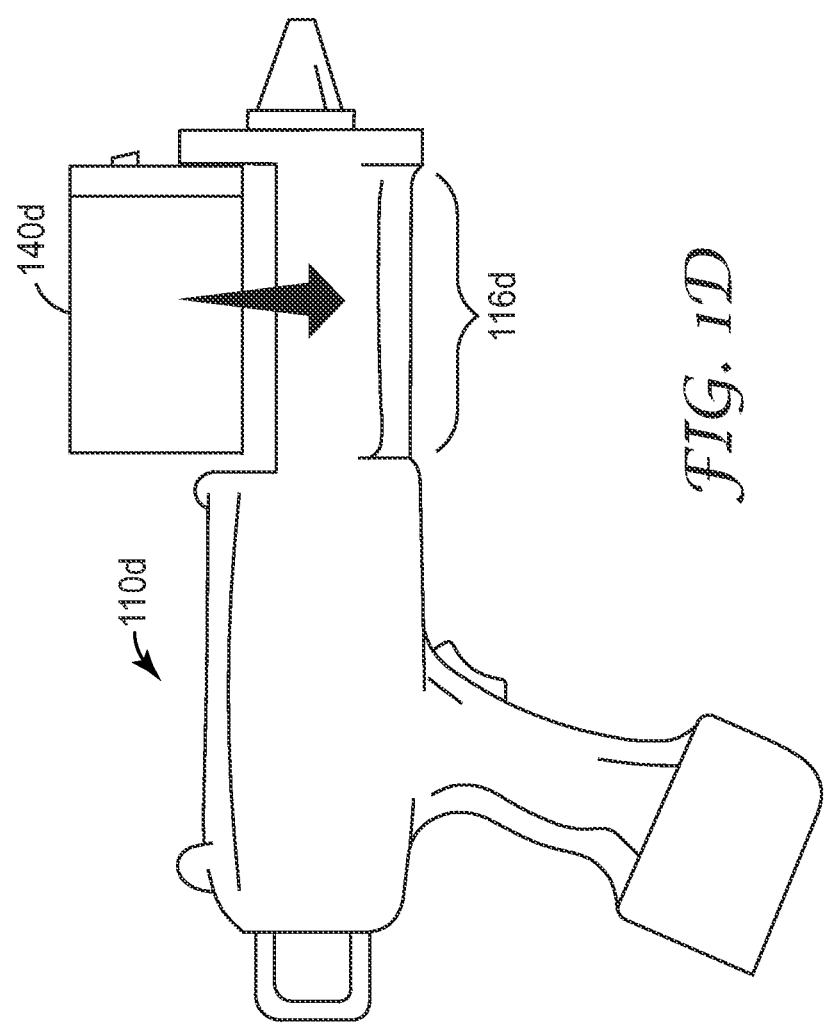

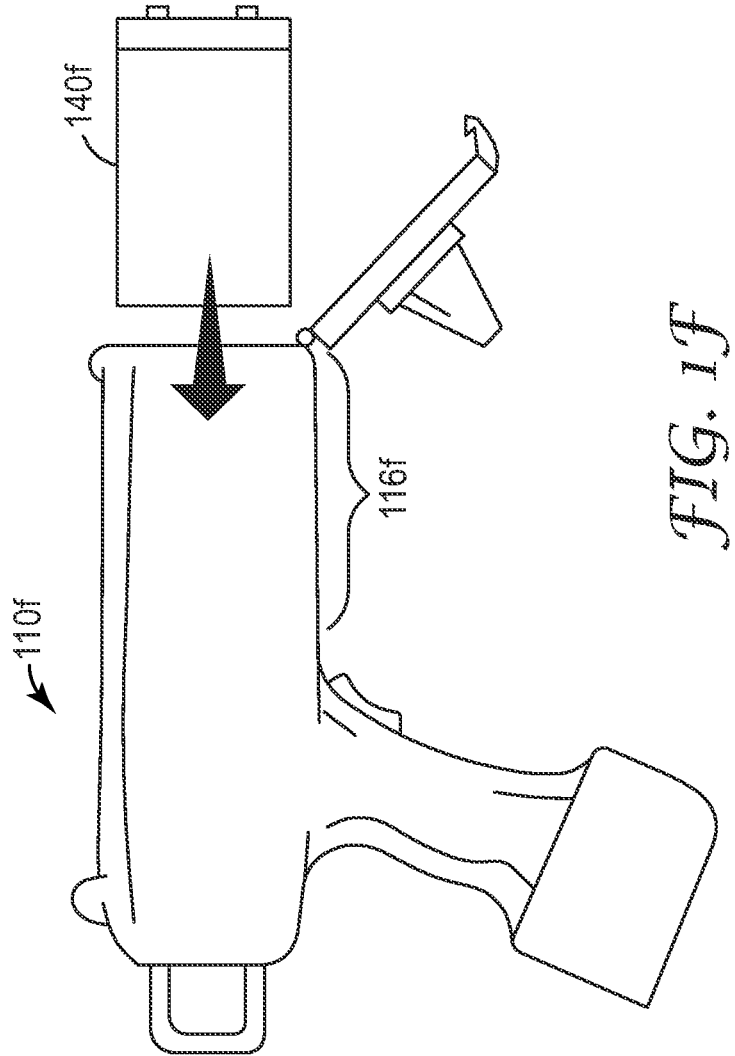

ABSTRACT

MIXING AND DISPENSING CURABLE MULTI-COMPONENT MATERIALS

RELATED APPLICATIONS

The present application claims the benefit under 35 U.S.C. §119(e) of U.S. Provisional Application Ser. No. 60/870,264, titled DEVICES AND METHODS FOR MIXING AND DISPENSING CURABLE MULTI-COMPONENT MATERIALS, filed on Dec. 15, 2006 and of U.S. Provisional Application Ser. No. 60/973,624, titled MIXING AND DISPENSING CURABLE MULTI-COMPONENT MATERIALS, filed on Sep. 19, 2007, both of which are hereby incorporated by reference in their entireties.

The present invention relates generally to the field of mixing and dispensing mixed materials. More particularly, the present invention relates to devices and methods for mixing and dispensing curable multi-component materials with highly disparate volumetric ratios, significantly different viscosities, extreme viscosities, etc.

The mixing and dispensing of multi-component materials offers a number of challenges, particularly for those materials that begin to cure or otherwise have a limited pot life after mixing. Among the issues that arise in such situations are accurate control over volumetric ratios of the various components making up the mixed material. The volumetric ratio of components in the mixed material may affect the rate at which the material cures, its ultimate strength, viscosity, longevity, etc. As such, control over the component to component ratio may be important.

Another issue is complete mixing of the components—if the mixing is inadequate, the uniformity of the resulting mixed material may be degraded. Still another potential issue is the introduction of air into the mixed material. In many instances (particularly with higher viscosity materials), air introduced into the mixed material during the mixing process may not be able to escape, which may result in suboptimal mixed material with entrapped air located therein.

Another potential issue in the mixing of components is the introduction of foreign matter (e.g., dirt, etc.) into the mixed material. This may particularly troublesome when the components may be mixed on previously used equipment that has been inadequately cleaned.

One particular area in which many of these problems may arise is in connection with automotive body repair materials in which reactive components (such as a hardener and filler) are mixed to form a body filler that can be used in the repair of vehicle body panels. Typically, the components of body fillers in use today are manually mixed by a technician who manually deposits (using, e.g., a hand tool) an approximate amount of filler obtained from an open container onto a mixing platform, followed by the addition of an approximate amount of hardener onto the mixing platform. The two components are then manually mixed by a technician using a tool such as, e.g., a squeegee. After mixing, the technician then applies the body filler to a vehicle. The technician typically uses abrasive articles such as sandpaper to form and shape the body repair materials to match the contours of the original article. This process may be repeated two or more times until the damaged area of the vehicle is sufficiently filled and the contour of the original article is matched.

This approach suffers from a number of the problems discussed above. For example, the amounts of the components are typically dispensed based on the judgment of the technician. As a result, the filler:hardener ratio between mixed batches can vary significantly. This may be particularly true if the ratio is larger, e.g., 10:1, 20:1 or even higher.

The variations in the filler to hardener ratio can affect the working time of the mixed body filler material. Too much hardener can result in body filler that cures too fast to allow sufficient working time, while too little hardener can result in body filler material that cures slower than desired. Excessive hardener can result in cracks forming in the body filler over time. In some body fillers, the hardener contains peroxide and/or a plasticizer. These materials may stain subsequently applied paint layers—especially if they are added in excessive amounts.

Another issue that may potentially be raised with manual mixing of body fillers is incomplete mixing of the filler and hardener which can result in uneven curing of the body filler. This issue may be more pronounced if, e.g., the viscosities of the filler and hardener are significantly different and/or the amount of body filler being mixed is relatively large.

Manual mixing of body filler may also result in air becoming trapped in the body filler. The entrapped air can, in some instances, form pinholes in the finished repair that require the addition of a glaze or other material to fill the pinholes during the repair process.

In addition to entrapped air, manual mixing can also result in the introduction of foreign matter (e.g., dirt, pieces of cured body filler, etc.) into the body filler if the surface and tools used to perform the mixing are not clean before mixing. This foreign matter can cause streaking as the technician tries to smooth the body filler on the repair site.

SUMMARY OF THE INVENTION

The present invention provides methods, apparatus, devices and systems for mixing and dispensing multi-component materials. The mixing and dispensing are preferably performed using a mobile, enclosed dispenser that can be used to advantageously supply a mixed multi-component material at the point of use. In some embodiments, the components to be mixed into the multi-component material may be supplied in cartridges to potentially simplify changeovers between different multi-component materials.

Among the potential advantages of the methods, apparatus, devices, and systems of the present invention is the ability to use one mixer/dispenser to handle a wide variety of input components to form the different multi-component materials that may be needed. The components may exhibit significantly different viscosities and may need to be mixed in significantly varying ratios. It is preferred, however, that the mixer/dispensers and methods of the invention be capable of providing multi-component materials that are appropriately mixed in spite of the variations in input materials.

The present invention may provide advantages where, for example, the volumetric ratio between the two or more components to be mixed to form different multi-component materials varies widely—from 1:1 or greater, 2:1 or greater, 10:1 or greater, 20:1 or greater, 40:1 or greater, 50:1 or greater, etc. The methods and devices of the present invention may preferably adapt to the mixing of different multi-component materials whose components are mixed in such different volumetric ratios with limited operator intervention.

The present invention may also provide advantages where the component materials have viscosity ratios that can vary widely. The methods and devices of the present invention may preferably be capable of mixing and dispensing multi-component materials made from two or more components whose viscosity ratios are, for example, 1:1 or higher (e.g., about equal), 2:1 or higher, 3:1 or higher, 4:1 or higher, 5:1 or higher, 10:1 or higher, 20:1 or higher, 50:1 or higher, or even 100:1 or higher. As with the variations in volumetric ratios, the methods and devices of the present invention may adapt to the mixing of different multi-component materials whose components exhibit such different viscosity ratios with limited operator intervention.

Yet other potential advantages of the methods and devices of the present invention may be found in the ability of the methods and devices to be used to mix component materials into multi-component materials when the input components have widely varying viscosities. For example, the viscosity of at least one of the components may be 200,000 centipoise or less, 100,000 centipoise or less, 50,000 centipoise or less, 25,000 centipoise or less, or even 10,000 centipoise or less. These low viscosity components may need to be mixed with one or more components that have a relatively high viscosity, e.g., 200,000 centipoise or higher, 300,000 centipoise or higher, 1,000,000 centipoise or higher, 1,500,000 centipoise or higher, etc. Again, the methods and devices of the present invention may preferably adapt to the mixing of different multi-component materials whose components exhibit such widely varying viscosities with limited operator intervention.

As discussed in the preceding paragraphs, the methods and devices of the present invention may provide advantages in the mixing of components into multi-component materials where the input components are supplied in widely varying volumetric ratios, have widely varying viscosity ratios, and have widely varying viscosities. It should be understood that one potentially significant advantage of the methods and devices of the present invention is their ability to provide uniform and accurately mixed multi-component materials under various combinations of all of these characteristics.

For example, it may be preferred that a mixer/dispenser and methods of mixing as described herein be capable of mixing components that exhibit a combination of widely disparate viscosities such as a viscosity ratio of 10:1 where the lower viscosity component has a viscosity of 10,000 centipoise or less at volumetric ratios of 1:1 or higher to 50:1 or higher. In another exemplary combination, the same methods and devices may be capable of mixing and dispensing a multi-component material made from components with a similar viscosity (e.g., 100,000 centipoise±25,000 centipoise) at a variety of volumetric ratios ranging from 1:1 or higher to 50:1 or higher. In still another example, the mixer/dispenser and methods of the present invention may be used to mix two components with viscosities of 400,000 centipoise and 100,000 centipoise (a 4:1 viscosity ratio) at a volumetric ratio of 40:1 or higher (where the larger volume is provided by the component with the higher viscosity). In other words, the methods and devices of the present invention may preferably offer flexibility in the input components to a degree not provided by conventional mixing equipment.

In spite of the variable characteristics of the input components, the dispensers, cartridges and methods of the present invention may preferably be capable of providing uniformly mixed multi-component materials.

Although described in some instances in terms of viscosity, it should be understood that the components mixed and dispensed in accordance with the present invention may include any flowable materials, where a flowable material is a material capable of flowing into and mixing with one or more other flowable components introduced into a mixing chamber. Flowable materials may include, e.g., liquids, gases, pastes, gels, flowable solids (e.g., flowable particulate streams), etc.

It may be preferred that the dispensers of the present invention be mobile units where "mobile" as used in connection with dispensers herein means that the dispenser can be manipulated by a user to dispense the mixed multi-component material at a variety of selected locations. For example, if the dispenser is being used for vehicle body repair, the mobile dispenser can be moved around the vehicle or shop such that the outlet of the mobile dispenser is positioned to dispense mixed material directly onto the vehicle or any other selected location. Such a mobile dispenser can be differentiated from desktop or stationary dispensers commonly used in, e.g., the mixing and dispensing of dental restoratives, etc.

In some embodiments, the mobile dispensers of the present invention may include self-contained power sources in addition to discrete amounts of the components mixed to form the multi-component material. For example, where compressed air (or any other gas) is to be used as a power source, the dispenser may be connected to a self-contained source of the compressed air (e.g., one or more tanks mounted on a backpack, cart, vehicle, etc.). If the power source is electric energy, it may be provided by a portable self-contained power source such as, e.g., batteries, fuel cells, etc.

The components to be mixed into the multi-component material may also be provided in the dispenser in cartridges that are capable of being refilled from a larger source (e.g., a backpack-mounted refill system, cart-based refill system, etc.). In such a system, the user may repeatedly refill the cartridges (or reservoirs) in the dispenser from a larger (yet still mobile) source as components in the cartridges are mixed and dispensed as a multi-component material. Alternatively, when the materials are provided to the dispenser from a larger source, the materials may be directly added, thus eliminating the need for a cartridge.

Another potential advantage of the methods, apparatus and systems of the present invention may include the ability to mix components in a multi-component material in which one of the components includes hollow elements (such as glass microspheres, ceramic microspheres, etc.) entrained therein while significant numbers of the hollow elements in the mixed multi-component material retain their integrity (i.e., are not crushed). For example, in some instances at least 50% of the hollow elements in a given volume of the mixed multi-component material may retain their integrity. In other embodiments, it may be preferred that 75% or more (or even 90% or more) of the hollow elements in a given volume of the mixed multi-component material may retain their integrity. Examples of some potentially suitable curable multi-component materials that include hollow elements (in, e.g., the form of microspheres) may be described in U.S. patent application Ser. No. 11/688,004, filed Mar. 19, 2007.

Although it may be advantageous that hollow elements retain their integrity within the mixed multi-component material, another potential advantage of the methods and apparatus of the present invention is that the mixed multi-component material may be substantially free of air that might otherwise be entrained in the multi-component material during, e.g., manual mixing techniques. Such air is not contained within hollow elements (if present) and, as such, may provide the basis for pinholes and other defects when the multi-component material is applied to a surface and finished. It may be preferred, for example, that volume of mixed multi-component material (e.g., curable vehicle body repair material) manufactured according to the present invention include entrapped air in the amount of 5% or less, 2% or less, 1% or less, 0.5% or less, 0.25% or less (by volume)—where entrapped air is air that is not enclosed within any hollow elements (if present) in the multi-component material.

Still another potential advantage of the methods, apparatus and systems of the present invention may include the ability to mix and dispense multi-component material in an enclosed process in which the components are dispensed from containers directly into a mixing chamber and exit the mixing chamber for direct application to a selected location. If, for example, the multi-component material is body repair material, the mixed body repair material may be dispensed directly into a repair site from the mixing chamber where the repair site may be located on any vehicle or article as discussed herein.

In one aspect, the present invention provides a method for mixing curable multi-component materials. The method includes providing a mobile dispenser having a first container containing a volume of a first component, a second container containing a volume of a second component, the mobile dispenser further including a mixing device that has a mixing chamber having a first inlet, a second inlet and an outlet; feeding the first component from the first container to the mixing chamber through the first inlet; feeding the second component from the second container to the mixing chamber through the second inlet, wherein the volumetric ratio of the first component to the second component (or vice versa) in the mixing chamber is about 40:1 or higher, and wherein the viscosity of the first component in the mixing chamber is about 10,000 cps or higher, and further wherein the ratio of the first component viscosity to the second component viscosity is about 1:1 or higher; mixing the first component and the second component in the mixing chamber during the feeding to form a first curable multi-component material; and dispensing the first curable multi-component material comprising the first component and the second component from the mixing chamber outlet.

As one skilled in the art would appreciate, the mixing chamber could have only one inlet, rather than a first and second inlet.

The methods may further include one or more of the following features: the volumetric ratio of the first component to the second component (or vice versa) in the mixing chamber may be about 50:1 or higher; the viscosity of the first component in the mixing chamber may be about 200,000 cps or higher; the ratio of the first component viscosity to the second component viscosity may be about 3:1 or higher; etc.

In another aspect, the present invention may provide a method for mixing curable multi-component materials by providing a mobile dispenser comprising a first container containing a volume of a first component, a second container containing a volume of a second component, the mobile dispenser further comprising a mixing device that comprises a mixing chamber having a first inlet, a second inlet and an outlet; feeding the first component from the first container to the mixing chamber through the first inlet; feeding the second component from the second container to the mixing chamber through the second inlet, wherein the volumetric ratio of the first component to the second component (or vice versa) in the mixing chamber is about 5:1 or less, and wherein the viscosity of the first component in the mixing chamber is about 10,000 cps or less, and further wherein the ratio of the first component viscosity to the second component viscosity is about 10:1 or higher; mixing the first component and the second component in the mixing chamber during the feeding to form a first curable multi-component material; and dispensing the first curable multi-component material comprising the first component and the second component from the mixing chamber outlet.

In another aspect, the present invention may provide a method for mixing curable multi-component materials by providing a mobile dispenser comprising a first container containing a volume of a first component, a second container containing a volume of a second component, the mobile dispenser further comprising a mixing device that comprises a mixing chamber having a first inlet, a second inlet and an outlet; feeding the first component from the first container to the mixing chamber through the first inlet; feeding the second component from the second container to the mixing chamber through the second inlet, wherein the volumetric ratio of the first component to the second component (or vice versa) in the mixing chamber is about 5:1 or less, and wherein the viscosity of the first component in the mixing chamber is about 10,000 cps to about 200,000 cps, and further wherein the ratio of the first component viscosity to the second component viscosity is about 4:1 or higher; mixing the first component and the second component in the mixing chamber during the feeding to form a first curable multi-component material; and dispensing the first curable multi-component material comprising the first component and the second component from the mixing chamber outlet.

In another aspect, the present invention may provide a method for mixing curable multi-component materials by providing a mobile dispenser comprising a first container containing a volume of a first component, a second container containing a volume of a second component, the mobile dispenser further comprising a mixing device that comprises a mixing chamber having a first inlet, a second inlet and an outlet; feeding the first component from the first container to the mixing chamber through the first inlet; feeding the second component from the second container to the mixing chamber through the second inlet, wherein the volumetric ratio of the first component to the second component (or vice versa) in the mixing chamber is about 5:1 or less, and wherein the viscosity of the first component in the mixing chamber is about 200,000 cps or higher, and further wherein the ratio of the first component viscosity to the second component viscosity is about 2:1 or higher; mixing the first component and the second component in the mixing chamber during the feeding to form a first curable multi-component material; and dispensing the first curable multi-component material comprising the first component and the second component from the mixing chamber outlet.

In another aspect, the present invention may provide a method for mixing curable multi-component materials by providing a mobile dispenser comprising a first container containing a volume of a first component, a second container containing a volume of a second component, the mobile dispenser further comprising a mixing device that comprises a mixing chamber having a first inlet, a second inlet and an outlet; feeding the first component from the first container to the mixing chamber through the first inlet; feeding the second component from the second container to the mixing chamber through the second inlet, wherein the volumetric ratio of the first component to the second component (or vice versa) in the mixing chamber is about 5:1 to about 10:1, and wherein the viscosity of the first component in the mixing chamber is about 10,000 cps or less, and further wherein the ratio of the first component viscosity to the second component viscosity is about 5:1 or higher; mixing the first component and the second component in the mixing chamber during the feeding to form a first curable multi-component material; and dispensing the first curable multi-component material comprising the first component and the second component from the mixing chamber outlet.

In another aspect, the present invention provides a method for mixing curable multi-component materials by providing a mobile dispenser comprising a first container containing a volume of a first component, a second container containing a volume of a second component, the mobile dispenser further comprising a mixing device that comprises a mixing chamber having a first inlet, a second inlet and an outlet; feeding the first component from the first container to the mixing chamber through the first inlet; feeding the second component from the second container to the mixing chamber through the second inlet, wherein the volumetric ratio of the first component to the second component (or vice versa) in the mixing chamber is about 5:1 to about 10:1, and wherein the viscosity of the first component in the mixing chamber is about 10,000 cps or higher, and further wherein the ratio of the first component viscosity to the second component viscosity is about 2:1 or higher; mixing the first component and the second component in the mixing chamber during the feeding to form a first curable multi-component material; and
dispensing the first curable multi-component material comprising the first component and the second component from the mixing chamber outlet.

In another aspect, the present invention provides a method for mixing curable multi-component materials by providing a mobile dispenser comprising a first container containing a volume of a first component, a second container containing a volume of a second component, the mobile dispenser further comprising a mixing device that comprises a mixing chamber having a first inlet, a second inlet and an outlet; feeding the first component from the first container to the mixing chamber through the first inlet; feeding the second component from the second container to the mixing chamber through the second inlet, wherein the volumetric ratio of the first component to the second component (or vice versa) in the mixing chamber is about 10:1 to about 20:1, and wherein the viscosity of the first component in the mixing chamber is about 10,000 cps or less, and further wherein the ratio of the first component viscosity to the second component viscosity is about 3:1 or higher; mixing the first component and the second component in the mixing chamber during the feeding to form a first curable multi-component material; and dispensing the first curable multi-component material comprising the first component and the second component from the mixing chamber outlet.

In another aspect, the present invention provides a method for mixing curable multi-component materials by providing a mobile dispenser comprising a first container containing a volume of a first component, a second container containing a volume of a second component, the mobile dispenser further comprising a mixing device that comprises a mixing chamber having a first inlet, a second inlet and an outlet; feeding the first component from the first container to the mixing chamber through the first inlet; feeding the second component from the second container to the mixing chamber through the second inlet, wherein the volumetric ratio of the first component to the second component (or vice versa) in the mixing chamber is about 10:1 to about 20:1, and wherein the viscosity of the first component in the mixing chamber is about 10,000 cps to about 200,000 cps, and further wherein the ratio of the first component viscosity to the second component viscosity is about 2:1 or higher; mixing the first component and the second component in the mixing chamber during the feeding to form a first curable multi-component material; and dispensing the first curable multi-component material comprising the first component and the second component from the mixing chamber outlet.

In another aspect, the present invention provides a method for mixing curable multi-component materials by providing a mobile dispenser comprising a first container containing a volume of a first component, a second container containing a volume of a second component, the mobile dispenser further comprising a mixing device that comprises a mixing chamber having a first inlet, a second inlet and an outlet; feeding the first component from the first container to the mixing chamber through the first inlet; feeding the second component from the second container to the mixing chamber through the second inlet, wherein the volumetric ratio of the first component to the second component (or vice versa) in the mixing chamber is about 10:1 to about 20:1, and wherein the viscosity of the first component in the mixing chamber is about 200,000 cps or higher, and further wherein the ratio of the first component viscosity to the second component viscosity is about 1.5:1 or higher; mixing the first component and the second component in the mixing chamber during the feeding to form a first curable multi-component material; and dispensing the first curable multi-component material comprising the first component and the second component from the mixing chamber outlet.

In another aspect, the present invention provides a method for mixing curable multi-component materials by providing a mobile dispenser comprising a first container containing a volume of a first component, a second container containing a volume of a second component, the mobile dispenser further comprising a mixing device that comprises a mixing chamber having a first inlet, a second inlet and an outlet; feeding the first component from the first container to the mixing chamber through the first inlet; feeding the second component from the second container to the mixing chamber through the second inlet, wherein the volumetric ratio of the first component to the second component (or vice versa) in the mixing chamber is about 20:1 or higher, and wherein the viscosity of the first component in the mixing chamber is about 10,000 cps or less, and further wherein the ratio of the first component viscosity to the second component viscosity is about 2:1 or higher; mixing the first component and the second component in the mixing chamber during the feeding to form a first curable multi-component material; and dispensing the first curable multi-component material comprising the first component and the second component from the mixing chamber outlet.

In another aspect, the present invention provides a method for mixing curable multi-component materials by providing a mobile dispenser comprising a first container containing a volume of a first component, a second container containing a volume of a second component, the mobile dispenser further comprising a mixing device that comprises a mixing chamber having a first inlet, a second inlet and an outlet; feeding the first component from the first container to the mixing chamber through the first inlet; feeding the second component from the second container to the mixing chamber through the second inlet, wherein the volumetric ratio of the first component to the second component (or vice versa) in the mixing chamber is about 20:1 or higher, and wherein the viscosity of the first component in the mixing chamber is about 10,000 cps or higher, and further wherein the ratio of the first component viscosity to the second component viscosity is about 1:1 or higher; mixing the first component and the second component in the mixing chamber during the feeding to form a first curable multi-component material; and dispensing the first curable multi-component material comprising the first component and the second component from the mixing chamber outlet.

In another aspect, the present invention provides a cartridge apparatus for use in a mobile mixing dispenser, the cartridge apparatus comprising: a cartridge housing comprising a first cavity located within a housing and a second cavity located within the housing, wherein the first cavity and the second cavity extend from a base of the cartridge housing towards a dispensing end distal from the base; a first container located within the first cavity, the first container containing a first component of a curable multi-component material; a second container located within the second cavity, the second container containing a second component of the curable multi-component material; a mixer drive passageway defining a drive axis; and a rotatable drive shaft located within the mixer drive passageway.

The cartridge apparatus described in the preceding paragraph may include one or more of the following features: the base may be flat and the drive shaft does not protrude past the base such that the cartridge housing can stand on the base on a flat horizontal surface; the mixer drive passageway may be located between the first cavity and the second cavity; the curable multi-component material may be curable body repair material; the cartridge housing may include means for attaching a dynamic mixer to a delivery end of the housing, wherein the drive axis extends through the means for attaching.

In another aspect, the present invention may provide a cartridge apparatus for use in a mobile mixing dispenser, the cartridge apparatus comprising: a cartridge housing comprising a first cavity located within a housing, the first cavity comprising a first cross-sectional area transverse to a first axis that extends along a length of the first cavity, wherein the cartridge housing further comprises a second cavity located within the housing, the second cavity comprising a second cross-sectional area transverse to a second axis that extends along a length of the second cavity; a spacer sized to fit within the second cavity of the cartridge housing, wherein the spacer defines a spacer cross-sectional area that occupies 1% or more of the second cross-sectional area, and wherein the spacer defines an open cross-sectional area within the second cavity; a first container located within the first cavity, the first container containing a first component of a curable multi-component material; and a second container located within the open cross-sectional area of the of the second cavity, the second container containing a second component of the curable multi-component material.

In another aspect, the present invention provides a multi-component package for delivering two or more component materials to a mixing and dispensing device, the package comprising: a collapsible first container defining a first axis, wherein a first component is sealed within the first container; a collapsible second container defining a second axis, wherein a second component is sealed within the second container; a cap assembly attached to the first container and the second container, wherein the cap assembly comprises: a first cap attached to a first end of the first container, wherein the first cap defines a flow path through which the first component exits the first container and passes through the first cap; a second cap attached to the first end of the second container, wherein the second cap defines a flow path through which the second component exits the second container and passes through the second cap; and a mechanically interlocking connection between the first cap and the second cap connecting the first cap to the second cap.

In another aspect, the present invention provides a multi-component material dispenser comprising: a frame comprising a housing enclosure and an optional handle projecting from the housing enclosure, wherein the housing enclosure comprises a front end and a rear end, with a longitudinal axis extending between the front end and the rear end of the housing enclosure; a cartridge chamber located proximate the front end of the housing enclosure; a cartridge located in the cartridge chamber, wherein the cartridge comprises: a first cavity located within a housing, the first cavity comprising a first volume that defines a first axis; a second cavity located within the housing, the second cavity comprising a second volume that defines a second axis; a mixer drive passageway located between the first cavity and the second cavity, the mixer drive passageway defining a drive axis; first and second plungers operatively connected to the drive shaft, wherein rotation of the drive shaft advances the first plunger along the longitudinal axis through the first cavity and the second plunger along the longitudinal axis through the second cavity; a dynamic mixer optionally attached to the front end of the housing enclosure, the dynamic mixer comprising a first inlet in fluid communication with the first cavity and a second inlet in fluid communication with the second cavity, the dynamic mixer further comprising an outlet through which material exits the dynamic mixer after mixing; wherein the dispenser is mobile, hand-held and adapted to deliver mixed multi-component materials through the outlet of the dynamic mixer.

In another aspect, the present invention provides a multi-component material dispenser comprising: a frame comprising a housing enclosure and an optional handle projecting from the housing enclosure, wherein the housing enclosure comprises a front end and a rear end, with a longitudinal axis extending between the front end and the rear end of the housing enclosure; a cartridge chamber located proximate the front end of the housing enclosure; a plunger chamber comprising a plunger piston located therein, the plunger chamber adapted to receive compressed air from a compressed air source connected to the dispenser; first and second plungers operatively connected to the plunger piston, wherein movement of the plunger piston towards the front end of the housing enclosure advances the first plunger along the longitudinal axis through the first cavity and the second plunger along the longitudinal axis through the second cavity; an air motor operatively attached to the dispenser, the air motor adapted to receive compressed air from the compressed air source; and a dynamic mixer attached to the front end of the housing enclosure, wherein the dynamic mixer is operatively attached to the air motor through a mixer drive shaft, the dynamic mixer comprising a first inlet in fluid communication with the first cavity and a second inlet in fluid communication with the second cavity, the dynamic mixer further comprising an outlet through which material exits the dynamic mixer after mixing, and wherein the dispenser is mobile, hand-held and adapted to deliver mixed multi-component material continuously through the outlet of the dynamic mixer.

In another aspect, the present invention provides a curable multi-component material comprising a substantially homogeneous mixture of unsaturated polyester resin and a catalyst, wherein the mixture optionally includes hollow elements and/or styrene, wherein the volume of air not encapsulated by the hollow elements within the body repair material is 5% or less of the volume of the curable multi-component material.

In another aspect, the present invention may provide a method for mixing curable multi-component material by providing a mobile dispenser including a first container containing a fixed volume of a first component, a second container containing a fixed volume of a second component, and a mixing device that includes an enclosed mixing chamber with a first inlet, a second inlet and an outlet. The method may further include feeding the first component from the first container to the mixing chamber through the first inlet and feeding the second component from the second container to the mixing chamber through the second inlet. The volumetric ratio of the two components delivered to the mixing chamber may be 10:1 or greater and/or the viscosity ratio of the first component viscosity to the second component viscosity may be 10:1 or greater. Optionally, the viscosity of at least one of the components may be 100,000 centipoise or less and/or the viscosity of at least one of the components may be 200,000 or more. The method may further involve continuously mixing the first component and the second component in the mixing chamber during the feeding to form a curable multi-component material and dispensing the curable multi-component material from the mixing chamber outlet. The method may also involve purging the mixed curable multi-component material from the mixing chamber outlet at a selected time.

In another aspect, the present invention may provide a method for mixing curable multi-component material by providing a mobile dispenser including a first container containing a fixed volume of a first component, a second container containing a fixed volume of a second component, and a mixing device that includes an enclosed mixing chamber with a first inlet, a second inlet and an outlet. The method may further include feeding the first component from the first container to the mixing chamber through the first inlet and feeding the second component from the second container to the mixing chamber through the second inlet. The volumetric ratio of the components delivered to the mixing chamber may be 10:1 or greater and/or the viscosity ratio of the first component viscosity to the second component viscosity may be 10:1 or greater. The method may further involve continuously mixing the first component and the second component in the mixing chamber during the feeding to form a curable multi-component material and dispensing the curable multi-component material from the mixing chamber outlet.

In another aspect, the present invention may provide a method for mixing curable multi-component material by providing a mobile dispenser including a first container containing a fixed volume of a first component, a second container containing a fixed volume of a second component, and a mixing device that includes an enclosed mixing chamber with a first inlet, a second inlet and an outlet. The method may further include feeding the first component from the first container to the mixing chamber through the first inlet and feeding the second component from the second container to the mixing chamber through the second inlet. The viscosity ratio of the first component viscosity to the second component viscosity may be 100:1 or greater and the viscosity of at least one of the components may be 100,000 centipoise or less. Optionally, the viscosity of at least one of the components may be 200,000 or more. The method may further involve continuously mixing the first component and the second component in the mixing chamber during the feeding to form a curable multi-component material and dispensing the curable multi-component material from the mixing chamber outlet.

In another aspect, the present invention may provide a method for mixing curable multi-component body repair material by providing a mobile dispenser including a first container containing a fixed volume of a first component, a second container containing a fixed volume of a second component, and a mixing device that includes an enclosed mixing chamber with a first inlet, a second inlet and an outlet. The method may further include feeding the first component from the first container to the mixing chamber through the first inlet and feeding the second component from the second container to the mixing chamber through the second inlet. The volumetric ratio of the first component to the second component in the mixing chamber may be 40:1 or greater and the viscosity ratio of the components may be 10:1 or greater. Optionally, the viscosity of at least one of the components may be 100,000 centipoise or less and/or the viscosity of at least one of the components may be 200,000 or more. The method may further involve continuously mixing the first component and the second component in the mixing chamber during the feeding to form a curable multi-component material and dispensing the curable multi-component material from the mixing chamber outlet. The method may also involve purging the mixed curable multi-component material from the mixing chamber outlet at a selected time.

In another aspect, the present invention may provide a method for mixing different curable multi-component materials that includes providing a mobile dispenser having a first container containing a fixed volume of a first component, a second container containing a fixed volume of a second component, the mobile dispenser further including a mixing device that has an enclosed mixing chamber with a first inlet, a second inlet and an outlet. The method further includes feeding the first component from the first container to the mixing chamber through the first inlet and feeding the second component from the second container to the mixing chamber through the second inlet, wherein the volumetric ratio of the first component to the second component (or vice versa) in the mixing chamber is 1:1 or greater, and optionally wherein the viscosity of the second component is 200,000 centipoise or less. The method further includes continuously mixing the first component and the second component in the mixing chamber during the feeding to form a first curable multi-component material and dispensing the first curable multi-component material including the first component and the second component from the mixing chamber outlet. The method may also include optionally replacing the first container in the dispenser with a third container containing a fixed volume of a third component and optionally replacing the second container in the dispenser with a fourth container containing a fixed volume of a fourth component. The method may further include optionally feeding the third component from the third container to the mixing chamber through the first inlet; optionally feeding the fourth component from the fourth container to the mixing chamber through the second inlet, wherein the volumetric ratio of the third component to the fourth component (or vice versa) in the mixing chamber is 40:1 or greater, and wherein the viscosity ratio of the third component viscosity to the fourth component viscosity (or vice versa) is 1:1 or greater, and optionally wherein the viscosity of the fourth component is 100,000 centipoise or less. The method may further include continuously mixing the third component and the fourth component in the mixing chamber during the feeding to form a second curable multi-component body repair material and dispensing the second curable multi-component material including the third component and the fourth component from the mixing chamber outlet. The method may still further include optionally purging the mixed first or second curable multi-component materials from the mixing chamber outlet at one or more selected times.

In another aspect, the present invention may provide a cartridge apparatus for use in a mobile mixing dispenser, the cartridge apparatus including a cartridge housing having a first cavity located within a housing, the first cavity having a first cross-sectional area transverse to a first axis that extends along a length of the first cavity, wherein the cartridge housing further includes a second cavity located within the housing, the second cavity having a second cross-sectional area transverse to a second axis that extends along a length of the second cavity; a spacer sized to fit within the second cavity of the cartridge housing, wherein the spacer defines a spacer cross-sectional area that occupies 1% or more of the second cross-sectional area, and wherein the spacer defines an open cross-sectional area within the second cavity; a first container located within the first cavity, the first container containing a first component of a curable multi-component material; and a second container located within the open cross-sectional area of the of the second cavity, the second container containing a second component of the curable multi-component material.

In another aspect, the present invention may provide a multi-component package for delivering two or more component materials to a mixing and dispensing device, the package including a collapsible first container having a tubular shape defining a first axis, wherein a first component is sealed within the first container; a collapsible second container having a tubular shape defining a second axis, wherein a second component is sealed within the second container; and a cap assembly attached to the first container and the second container. The cap assembly includes a first cap attached to a first end of the first container, wherein the first cap defines a flow path through which the first component exits the first container and passes through the first cap; a second cap attached to the first end of the second container, wherein the second cap defines a flow path through which the second component exits the second container and passes through the second cap; and a mechanically interlocking connection between the first cap and the second cap connecting the first cap to the second cap such that the first axis and the second axis are generally parallel with each other.

In another aspect, the present invention may provide a multi-component material dispenser that may include a frame having a barrel and an optional handle projecting from the barrel, wherein the barrel has a front end and a rear end, with a longitudinal axis extending between the front end and the rear end of the barrel; a cartridge chamber located proximate the front end of the barrel; and a cartridge optionally located in the cartridge chamber. The cartridge may include a first cavity located within a housing, the first cavity having a tubular first volume that defines a first axis; a second cavity located within the housing, the second cavity having a cylindrical second volume that defines a second axis, wherein the first axis and the second axis are generally parallel to each other; and an optional mixer drive passageway located between the first cavity and the second cavity, the mixer drive passageway defining a drive axis that is generally parallel to the first axis and the second axis. The dispenser may also include first and second plungers operatively connected to the drive shaft, wherein rotation of the drive shaft advances the first plunger along the longitudinal axis through the first cavity and the second plunger along the longitudinal axis through the second cavity. A dynamic mixer may optionally be attached to the front end of the barrel, the dynamic mixer including a first inlet in fluid communication with the first cavity and a second inlet in fluid communication with the second cavity, the dynamic mixer further including an outlet through which material exits the dynamic mixer after mixing. The dispenser may preferably be a mobile, hand-held dispenser adapted to deliver mixed multi-component material continuously through the outlet of the dynamic mixer.

In another aspect, the present invention may provide a multi-component material dispenser that may include a frame having a barrel and an optional handle projecting from the barrel, wherein the barrel has a front end and a rear end, with a longitudinal axis extending between the front end and the rear end of the barrel. The dispenser may further include a cartridge chamber located proximate the front end of the barrel; a plunger chamber having a plunger piston located therein, the plunger chamber adapted to receive compressed air from a compressed air source connected to the dispenser; first and second plungers operatively connected to the plunger piston, wherein movement of the plunger piston towards the front end of the barrel advances the first plunger along the longitudinal axis through the first cavity and the second plunger along the longitudinal axis through the second cavity; an optional air motor operatively attached to the dispenser, the air motor adapted to receive compressed air from the compressed air source; an optional dynamic mixer attached to the front end of the barrel, wherein the dynamic mixer is operatively attached to the air motor through a mixer drive shaft, the dynamic mixer having a first inlet in fluid communication with the first cavity and a second inlet in fluid communication with the second cavity, the dynamic mixer further including an outlet through which material exits the dynamic mixer after mixing. The dispenser may also include an optional purge line operatively connected to the compressed air source and the mixing chamber, wherein compressed air directed into the mixing chamber through the purge line forces material in the mixing chamber out of the mixing chamber through the outlet; an optional first one-way valve located between the mixing chamber and the first inlet, the first one-way valve operating to close in response to the delivery of compressed air to the mixing chamber through the purge line; and an optional second one-way valve located between the mixing chamber and the second inlet, the second one-way valve operating to close in response to the delivery of compressed air to the mixing chamber through the purge line. The dispenser may provide a mobile, hand-held dispenser adapted to deliver mixed multi-component material continuously through the outlet of the dynamic mixer.

In another aspect, the present invention provides a curable body repair material in the form of a substantially homogeneous mixture of unsaturated polyester resin and a catalyst, wherein the mixture optionally includes hollow elements and/or styrene, and wherein the volume of air not encapsulated by any hollow elements within the body repair material is 5% or less of the volume of the curable body repair material. A technician may then apply the body repair material to a repair site (e.g., a vehicle). During and/or after curing the technician may shape the body repair material using, e.g., abrasive articles such as sandpaper, to form and shape the body repair material to match the contour of the original article. This process may be repeated two or more times until damaged site is sufficiently filled and the contour matches the original.

It should be noted that the methods and articles described herein may also be used to dispense materials that are not curable, but simply require mixing.

The above summary is not intended to describe all of the features or advantages of the present invention. Rather, a more complete understanding of the invention will become apparent and appreciated by reference to the following Detailed Description of Exemplary Embodiments and claims in view of the accompanying figures of the drawing.

BRIEF DESCRIPTIONS OF THE VIEWS OF THE DRAWING

The present invention will be further described with reference to the figures of the drawing, wherein:

FIG. 1 is a cross-sectional view of one exemplary dispenser that may be used to mix and dispense multi-component materials in accordance with the present invention.

FIG. 1B is a partial cross-sectional view of a portion of a dispenser depicting a variety of exemplary plunger reverse mechanisms.

FIG. 1C is a flow diagram illustrating one purging system that may be used in connection with the present invention.

FIGS. 1D-1G depict some exemplary alternative approaches to loading cartridges into the dispenser of FIGS. 1 & 1A.

DETAILED DESCRIPTION OF EXEMPLARY EMBODIMENTS

Figure 1A:
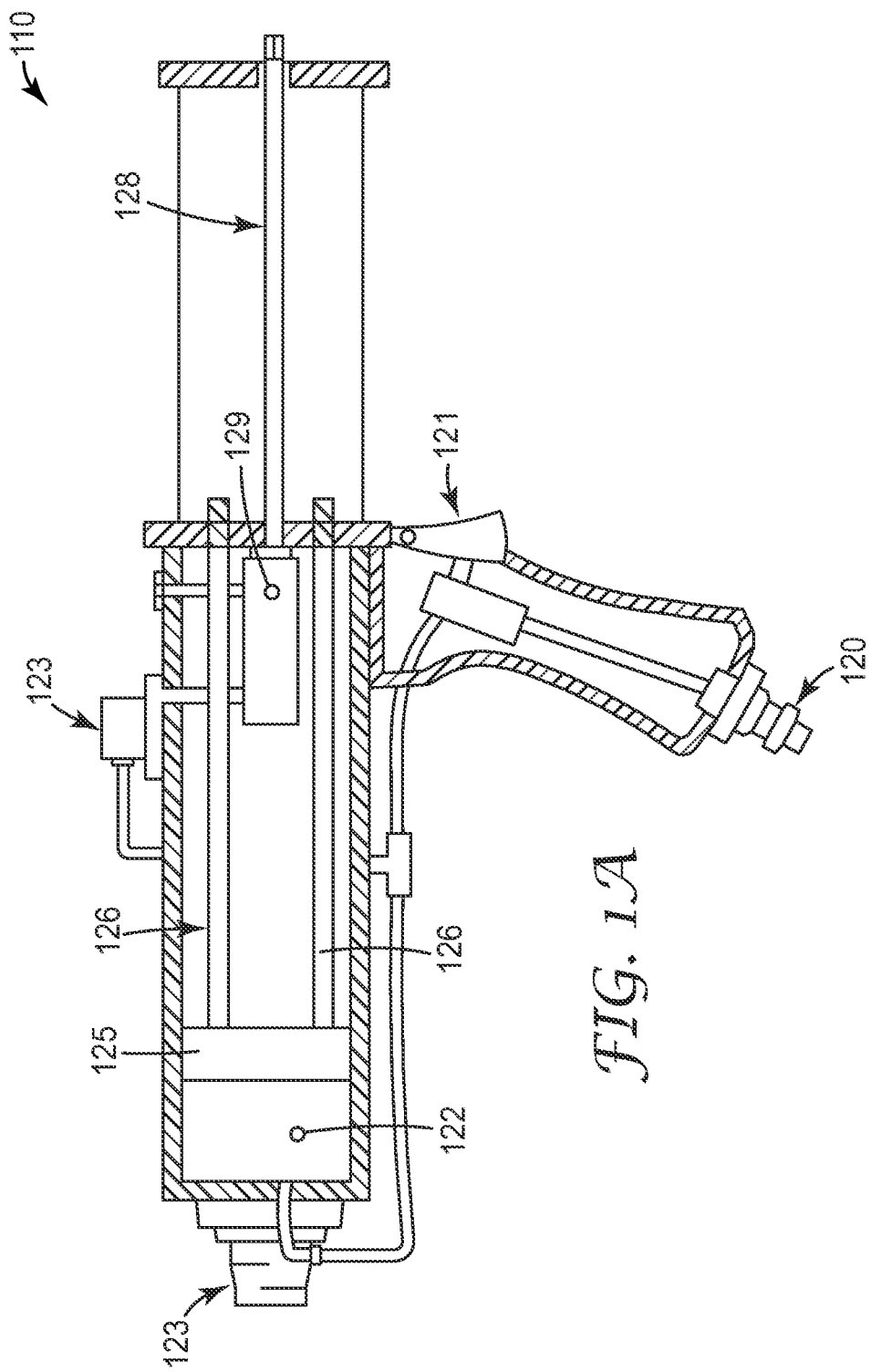
FIG. 1A is a cross-sectional view of another exemplary dispenser that may be used to mix and dispense multi-component materials in accordance with the present invention.

In the following detailed description of exemplary embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

The present invention includes methods of mixing two or more components to form a curable multi-component material and dispensing of the mixed material. Although the exemplary embodiments described below include two components, the present invention may be used to provide a multi-component material that includes three or more components that are mixed and dispensed from a single system.

It is preferred that the mixing be performed in an enclosed system in which the components are dispensed from containers directly into a mixing chamber with little or no exposure to the surrounding environment. The mixed multi-component material is then ejected from the mixing chamber after mixing for use. It may be preferred that the path for components from the containers to the mixing chamber be sealed such that no air is delivered or present in the mixing chamber (other than air or other gases contained in hollow elements that may be provided in one or more of the components).

The term "curable" as used herein refers to reactive multi-component materials that cure (i.e., irreversibly solidify) after mixing of the components used in the multi-component material. The curing may be assisted by or require the application of heat and/or other sources of energy, such as E-beam, ultraviolet light, visible light, etc. In another alternative, the curing may be assisted by contact with a chemical catalyst, moisture, etc. Other curing mechanisms may be used in place of or in addition to those explicitly identified herein. The irreversible solidification may involve polymerization, crosslinking, or both. Before curing, it may be preferred that the curable multi-component material be sufficiently malleable and/or flowable such that it can be manipulated into a variety of shapes, smoothed, troweled, sprayed, etc.

Among the potential advantages of the present invention include the ability to uniformly mix components in which the volumetric ratio is relatively diverse, e.g., 1:1 or greater, 10:1 or greater, 20:1 or greater, 40:1 greater, 50:1 or greater, etc. In addition, mixing components with relatively high volumetric ratios can be complicated when those components have relatively diverse viscosity ratios, e.g., 1:1 or higher (e.g., about equal), 2:1 or higher, 5:1 or higher, 10:1 or higher, 20:1 or higher, 50:1 or higher, 100:1 or higher, or even 1000:1 or higher. The exemplary apparatus and devices described herein may address these issues along with others to provide an effective solution to the issues faced when mixing and dispensing multi-component materials with these properties.

The methods and apparatus of the present invention may be used to mix and dispense a wide variety of curable multi-component materials such as, e.g., epoxies, urethanes, silicones, vinyl esters, polyesters, polysulfides, etc. One class of multi-component materials that may benefit from use of the methods and apparatus of the present invention are curable body repair materials used in the repair of damaged vehicles and other equipment (e.g., cars, trucks, watercraft, windmill blades, aircraft, recreational vehicles, bathtubs, storage containers, pipelines, etc.). Curable body repair materials may preferably include two reactive components (e.g., filler and hardener) which are mixed together to form the curable body repair material. The volumetric ratio of the reactive components may be in the range of, e.g., 1:1 or higher (where higher is, e.g., 2:1, 3:1, etc.) for epoxy or urethane compounds and may be 20:1 or higher for unsaturated polyesters with a peroxide catalyst as a hardener. The viscosities of the two reactive components may be the same or different—making the mixing and dispensing of curable body repair material a challenging task that is, as a result, typically performed by hand. Such hand mixing, as discussed above, can result in entrapped air, incomplete mixing and variability in the volumetric ratio of the components.

The filler component of curable body repair materials may include, e.g., unsaturated polyester resin, talc, clays, pigments, dispersion stability additives (e.g., amorphous silica), glass microspheres, etc. The filler may also include unsaturated reactive diluents such as, e.g., styrene. The filler may also include additives to impart adhesion of the curable multi-component material to common repair surfaces such as, e.g., aluminum, galvanized steel, E-coats, primers, paints, etc. The adhesion additives may have, e.g., anhydride functionality, silane functionality, or amine functionality, and the adhesion additives may or may not be incorporated into the base resin. The viscosity of the filler may be greater than 100,000 centipoise. The filler may also incorporate, e.g., accelerants for the curing process. The corresponding hardener component of curable body repair material may be a polyester plasticizer blended with a catalyst (e.g., peroxide), pigment, dye, etc. The consistency of the hardener can range from a paste-like to water-like consistency—although it may be less viscous than the corresponding filler. In some body repair materials, the hardener may have a viscosity of 200,000 centipoise or less.

If mixing and dispensing curable body repair materials, the dispensers of the present invention may dispense the mixed curable body repair material onto a separate squeegee or other tool for application to the surface to be repaired. Alternatively, the dispenser may be used to deliver the mixed curable body repair material directly to the repair site. In some instances, the dispenser may be used to deliver a thin layer of curable body repair material followed by a thicker layer before the initial thin layer cures (what may be referred to as a "wet-on-wet" application). In some methods, the repair surface is sanded, and/or primed before the curable body repair material is delivered. In some embodiments, the curable body repair material itself may act as a prime layer.

FIG. 1 depicts one exemplary dispenser 10 that includes a pistol-grip handle 12 extending from a central housing 14. The depicted dispenser 10 includes a power source 20 (e.g., battery) operably connected to a motor 22 through a trigger switch 21. The dispenser 10 also includes a compartment 16 in which the containers 42 and 44 holding the components to be mixed are located. The containers used to supply components of the multi-component materials may preferably contain fixed volumes of the components where, for example, the volume of the component in the container is 5000 cubic centimeters or less, or in some instances 2000 cubic centimeters or less.

The motor 22 is operably connected to a ball screw 24 such that the motor 22 rotates the screw 24 about axis 11. As the screw 24 rotates, it drives a follower 25 along the axis 11, with directional control over movement of the follower 25 along the axis 11 being obtained by, e.g., selecting the direction of rotation of the screw 24.

The dispenser 10 also includes plungers 26 operably connected to the follower 25 such that as the follower 25 moves towards the compartment 16, plungers 26 advance into the compartment 16 to force the components in the containers 42 and 44 into a mixing device 30 attached to the housing 14.

The containers 42 and 44 may preferably be arranged such that a flow path is established from the containers 42 and 44 into the mixing device 30. In the depicted embodiment, material from container 42 passes through flow path 43 into the mixing device 30 and material from container 44 passes through flow path 45 into the mixing device 30.

If the mixing device 30 is a dynamic mixer including one or more movable elements within a mixing chamber (as is the mixer 30 depicted in FIG. 1), then the dispenser 10 also preferably includes components to operate the dynamic mixer. In the embodiment depicted in FIG. 1, the dispenser 10 includes a mixer drive shaft 28 that may preferably extend through the compartment 16 to reach the dynamic mixer 30. The mixer drive shaft 28 preferably couples with the dynamic mixer 30 to operate the moving elements of the mixer 30.

In addition to the drive shaft 28, the dispenser 10 also includes an optional gearbox 29 operably coupled to both the lead screw 24 and mixer drive shaft 28. The gearbox 29 is preferably capable of adjusting the rotational speed of the mixer drive shaft 28 such that it differs from the rotational speed of the lead screw 24. In many instances, it may be preferred that the mixer drive shaft rotate faster than the screw 24 (although in some instances the opposite arrangement may be preferred). The gearbox 29 may provide a fixed increase in rotational speed or the gearbox 29 may be capable of selectively adjusting the relative rotational speeds of the screw 24 and mixer drive shaft 28.

A number of potential variations from the dispenser 10 may be provided in connection with the present invention. For example, rather than operating the plungers 26 and dynamic mixer 30 from a single motor, two or more separate motors may be used (which may eliminate the need for some elements such as, e.g., gearbox 29). Further, the mixer used in connection with the dispenser may be a static mixer, thus eliminating the need to provide power to operate the mixer.

In another variation, alternative mechanisms for driving plungers 26 may be used in place of the screw 24 and follower 25 depicted in connection with the dispenser 10. For example, the plungers 26 may be driven by a chain drive, rack and pinion, hydraulically, etc. In some instances, a motor 22 may still be used to operate the dispenser 10, but the motor 22 may be powered pneumatically from, e.g., an air compressor (although the pneumatic line connected to the dispenser 10 preferably does not prevent the dispenser from use as a "mobile" dispenser as discussed herein).

One alternative embodiment of a dispenser 110 is depicted in FIG. 1A. In the depicted embodiment, power to operate the dispenser 110 is provided using compressed air provided through a fitting 120 on the dispenser 110. Although compressed air may be preferably used, other suitable fluids may be substituted. Compressed air may, however, be preferred because it is commonly available in many facilities in which dispensers may be used. One potential advantage of a dispenser powered through the use of compressed air is that the device may present a significantly reduced fire hazard for use in areas where combustible materials (e.g., liquids, gases, particulates, etc.) pose a hazard.

In the depicted dispenser 110, compressed air from a source (not shown) is fed into fitting 120 and controlled using trigger 121 which feeds the compressed air to the dispenser 110. As the trigger 121 is activated, the compressed air is directed to a plunger chamber 122 and an air motor 129.

Delivery of compressed air into plunger chamber 122 moves piston 125 to which plungers 126 are attached. As the piston 125 moves to the right (in the view depicted in FIG. 1A), the plungers 126 advance to dispense components from the dispenser 110 as discussed in connection with dispenser 10 of FIG. 1. Delivery of compressed air to the air motor 129 causes the motor 129 to rotate mixer drive shaft 128 to operate an optional dynamic mixer (not shown).

It may be preferred that the delivery of compressed air to the plunger chamber 122 and the motor 129 be controlled by separate regulators 123 to allow for independent control over movement of the plungers 126 and the speed at which the motor 129 rotates the mixer drive shaft 128.

In some embodiments, it may be preferred that the power source used to operate the dispensers of the present invention may be self-contained. For example, if the power used is electric energy, it may be preferred that the power be supplied from batteries or another self-contained source of electric energy (e.g., fuel cell, etc.). If the power source is compressed gas, it may be preferred that the compressed gas be supplied in one or more tanks that may be mounted for movement (e.g., using a backpack, cart, vehicle, etc.).

Other potential features of the dispensers of the present invention may include, e.g., a stop mechanism such that advancement of the plungers may be prevented based on, e.g., pressure limits within the system, etc. The dispenser may also include an integral light source such that, e.g., the area to which the multi-component material is being delivered can be illuminated. The light source may or may not include the delivery of electromagnetic energy in wavelengths that are capable of enhancing the curing of the multi-component material being delivered by the dispenser.

Another optional feature that may be included in the dispenser systems and methods of the invention is a plunger reverse mechanism that reverses the travel of the plungers after they have been advanced to dispense the multi-component material. Reversal of the plungers can be helpful in relieving the residual pressure that may otherwise be exerted on the containers by the plungers (or the seals they drive) even after the plungers are no longer being actively driven (as they are during dispensing). Unless relieved, that residual pressure can lead to dripping and/or continued dispensing of the multi-component material after the plungers are no longer being actively driven.

Although plunger reverse mechanisms may be helpful in reducing unwanted dripping when dispensing is terminated, the reverse mechanisms may be particularly helpful in systems that use dynamic mixers. If the dispensing system uses a static mixer, the multi-component material that is dispensed after the plungers are no longer being actively driven (due to, e.g., residual pressure) is still mixed because the mixing device itself is not actively driven. If, however, the system uses a dynamic mixing device that is actively driven to assist in complete mixing of the multi-component material and that driven mixing device is no longer driven when the plungers are no longer driven, then the components that would continue to enter the mixing device due to residual pressure may not be completely mixed. If dispensing is restarted, then that portion of the multi-component material in the mixing device could be dispensed, despite its potentially incomplete mixing. A plunger reverse mechanism may, however, be useful to reduce or prevent the continued delivery of components to the mixing device due to residual pressure.

Plunger reverse mechanisms that reverse plunger travel may be implemented by a variety of structures/devices, some examples of which are depicted in connection with the dispenser 110*b* in FIG. 1B. Only a portion of the dispenser 110*b* is depicted in FIG. 1B and the potentially suitable plunger reverse mechanisms are all depicted on the dispenser 110*b*, although it should be understood that any one of the plunger reverse mechanisms alone may be suitable to accomplish the function of reversing the plungers when dispensing is terminated.

Among the features of the dispenser 110*b* depicted in FIG. 1B are the plunger chamber 122*b*, and motor 129*b* used to drive an optional mixer drive shaft (not shown). Also depicted in FIG. 1B is a regulator 123*b* used to deliver compressed gas to the plunger chamber 122*b* to drive the piston 125*b* (which is operatively connected to the plungers (not shown in FIG. 1B).

Among the plunger reverse mechanisms depicted in FIG. 1B is a plate and spring combination in which the dispenser 110*b* includes a plunger return rod 190*b* operatively attached to the piston 125*b* (although if a plunger return rod 190*b* is not provided as a part of the dispenser 10*b*, this mechanism could be used on one or more of the plungers themselves). As the piston 125*b* advances to the right to drive the plungers (not shown) to dispense component material, the plunger return rod 190b also advances. As a part of that advance, a plate 192b attached to the return rod 190b moves to the right until it contacts and at least partially compresses the spring (or other suitable resilient member) 191b. The bottom end 193b of the plate 192b then eventually reaches an obstruction which straightens the plate 192b (to a more vertical orientation in FIG. 1B) and allows the return rod 190b to continue advancing to the right. When the delivery of compressed gas to the chamber 122b is terminated and the pressure in the chamber 122b is reduced (by, e.g., a dump valve), upper end of the plate 192b is forced to the left such that it grips the return rod 190b. With the spring forcing the plate 192b to the left, the return rod 190b is driven slightly to the left by the spring 191b. As the return rod 190b is driven to the left, the piston 125b is also driven to the left and, in turn, plungers operatively connected to the piston 125b are also move left, removing pressure on the component material to reduce the likelihood of dripping.

Another exemplary plunger reverse mechanism depicted in FIG. 1B is a pressure relief valve 194b that is located between the plunger chamber 122b and the forward chamber 195b (where, in the depicted embodiment, the forward chamber 195b is the chamber into which the piston 125b advances). Both the plunger chamber 122b and the forward chamber 195b are preferably sealed such that, as the piston 125b advances due to increasing pressure within the plunger chamber 122b, pressure within the forward chamber 195b increases. The pressure increase within the forward chamber 195b may preferably be limited by a pressure relief valve 194b to selected pressure. When the delivery of compressed gas to the plunger chamber 122b is terminated and the pressure in the plunger chamber 122b is reduced (by, e.g., a dump valve), the piston 125b is preferably forced to the left by the pressure built up within the forward chamber 195b. As the piston 125b is driven to the left by the pressure in the forward chamber 195b, the plungers (not shown) operatively connected to the piston 125b are also move left, removing pressure on the component material to reduce the likelihood of dripping.

Still another exemplary plunger reverse mechanism depicted in FIG. 1B is the use of a spring 196b (or other suitable resilient member) located forward of the piston 125b such that advancement of the piston 125b to drive the plungers (not shown) compresses or deforms the spring 196b. When the delivery of compressed gas to the plunger chamber 122b is terminated and the pressure in the plunger chamber 122b is reduced (by, e.g., a dump valve), the piston 125b is preferably forced to the left by the spring 196b. As the piston 125b is driven to the left by the spring 196b, the plungers (not shown) operatively connected to the piston 125b are also move left, removing pressure on the component material to reduce the likelihood of dripping.

Yet another exemplary embodiment of a plunger reverse mechanism includes the use of pressure dump valve 198b located on the piston 125b (or in another suitable location) and a sealed forward chamber 195b into which the piston 125b advances. When a trigger (or other actuator) used to deliver compressed gas into the plunger chamber 122b is released, the pressurized gas within the plunger chamber 122b (or at least a portion thereof) is delivered to the forward chamber 195b through the valve 198b. The combination of an increase in pressure within advance chamber 195b and decrease in pressure within the plunger chamber 122b preferably drives the piston 125b to the left. As the piston 125b is driven to the left by the pressure in advance chamber 195b, the plungers (not shown) operatively connected to the piston 125b also move left, removing pressure on the component material to reduce the likelihood of dripping.

Still other potential alternatives may include, e.g., the use of cartridges that incorporate a mixer drive shaft that couples with the mixing device at the delivery end and that couples with a drive shaft from a motor of the dispenser as discussed herein. As a result, the need for a separate drive shaft traversing, e.g., the cartridge compartment 16, may be eliminated. In another alternative, the drive shaft may remain a part of the dispenser, but may be retractable to facilitate replacement of the cartridges and/or mixer devices.

Another potential alternative may involve the use of refillable containers in connection with a larger, bulk source of the components to be mixed into the multi-component material. The bulk sources may still preferably be somewhat mobile. For example, the bulk component sources may be provided in, e.g., a backpack carrier, on a cart, on a vehicle, etc. such that they can be moved with a user at, e.g., a worksite, manufacturing facility, etc. In use, the containers in the dispenser may be periodically refilled from the mobile bulk component sources as the components in the containers are mixed and dispensed in the form of the multi-component material.

In yet other potential alternatives, the dispensers of the present invention may be adapted to use existing equipment to drive the plungers and/or mixer drive shaft. Such existing equipment may include, e.g., electric drills, air wrenches, etc.

Another optional feature that may be incorporated into the dispensers and/or methods of the invention is the use of thermal control apparatus to control the temperature of one or more of the components before mixing and/or the multi-component material during and/or after mixing. Control over temperature may be used to, e.g., control the curing rate, viscosity, and other properties of the components and/or mixed multi-component material. For example, heating may (in some systems) be used to increase the curing rate, cooling may (in some systems) be used to reduce the curing rate, heating may be used to decrease viscosity of some materials, etc.

The thermal control may be accomplished by the use of any suitable thermal control apparatus, e.g., electrical resistance heaters, Peltier elements, chilled fluids (e.g., water), fans, etc. The temperature control may be performed on the components in the containers or before the components reach the mixing device. Alternatively, the temperature control may be performed while the components are located in the mixing device. In yet another alternative, the temperature of the mixed multi-component material may be controlled as it exits the mixing device and/or dispenser.

In some dispensers and/or methods of the invention, it may be useful to allow for some variability between the ratio of the components being mixed. Control over the exact ratio of the components making up the mixed multi-component material may be used to effect a variety of changes. Adjusting the ratio of the components making up the mixed multi-component material may change, for example, the cure rate of the mixed multi-component material, one or more physical properties of the cured multi-component material (e.g., hardness, elasticity, density, electrical conductivity, thermal conductivity, opacity, etc.), the viscosity of the multi-component material (as dispensed), etc.

The component ratio adjustment may be made by any suitable technique or apparatus. One example may be the use of a dumping valve located between the source of at least one of the components and the mixing device used to mix the components to form the mixed multi-component material. The dumping valve may be binary (i.e., it may be either open or closed), adjustable between multiple discrete settings, or it may be infinitely adjustable between fully closed and fully open positions. It may be preferred, but not required, that the component passing through the dumping valve be collected in a reservoir (alternatively, the component passing through the dumping valve may be allowed to pass onto the floor or other collection point).

In still another alternative to controlling the ratio of the components mixed to form the multi-component material, the plungers used to deliver material from the different containers may be advanced independently of each other such that the volumetric ratio between the components in the containers 42 and 44 in the mixed multi-component material delivered by the dispenser 10 may be controlled (at least in part) by the rate at which the plungers advance.

Other features that may optionally be provided in connection with the dispensers of the present invention may include, e.g., hooks or other features (e.g., stands, etc.) to support the dispenser before, during or after use, shoulder straps to support some of the weight of the dispenser during use (the shoulder straps may include features to store additional cartridges, containers, mixing devices, flow shaping attachments, batteries, etc.), protection for any compressor fittings on the dispenser, protection for any controls on the dispenser, etc.

Another feature that may be included in connection with dispensers of the present invention is a purge function that may be used to clear the mixed multi-component material from the mixing chamber after a selected amount of the mixed multi-component material has been produced. The purging may preferably force the mixed multi-component material out of the mixing chamber through its outlet. Purging may be used to clear the multi-component material to allow re-use of the mixing device that would not be possible if, e.g., the curable multi-component material cured within the mixing chamber.

The purging may take a number of forms. In some instances the mixing chamber may be purged by delivering only one or more components to the mixing chamber that do not result in a curable multi-component material. For a two-component multi-component material, only one of the components may be delivered to the mixing chamber until all of the mixed multi-component material is purged from the mixing chamber (in essence forced out by the single component). A dispenser adapted to perform such a purge technique may preferably have plungers (or other mechanisms) that can be independently operated such that the selected component can be fed into the mixing chamber while the other component (or components) are not.

In another purging alternative, the mixing chamber may be purged using another flowable material such as, e.g., compressed air, water, solvents, etc. If the dispenser is powered (at least in part) by compressed air, it may be preferred that the purging be performed using compressed air. FIG. 1C depicts a flow diagram illustrating one potential approach to the use of compressed air as a purging material as well as the providing the energy required to drive plungers and a motor operating a mixer drive shaft. In the system depicted in FIG. 1C, the compressed air source 220 may be directed through a valve 221 that normally allows the compressed air to reach the plunger chamber 222 and an air motor 229 operating a mixer drive shaft. When actuated, however, the valve 221 may direct compressed air through a purge line that enters the mixing chamber 230 to force mixed multi-component material located therein out of the mixing chamber through its outlet. Because the mixing chamber includes inlets through which the components to be mixed enter the mixing chamber, it may be advantageous to provide one-way valves at those inlets to reduce or prevent the compressed air from entering the containers from which the components are delivered to the mixing chamber.

The dispenser and any containers/cartridges used in connection with the present invention may incorporate radio-frequency identification equipment (RFID), barcodes, or other indicia or indicators of the characteristics of the material to be mixed to provide potentially automated control over material mixing, delivery, etc. The identification of the components using some form of indicia may be used in a variety of ways. In some instances, the rate at which the mixed multi-component material is delivered may be modified (e.g., increased, decreased, etc.), the speed of a dynamic mixing element may be modified (e.g., increased, decreased, etc.), etc. Examples of some potential interlock systems and methods using identification indicia in connection with a dispenser may be described in, e.g., U.S. Pat. No. 7,040,566 B1 (Rodrian et al.), titled DISPENSER WITH MATERIAL-RECOGNITION APPARATUS AND MATERIAL-RECOGNITION METHOD.

As discussed herein, it may be preferred that the dispensers of the present invention be mobile such that the dispenser can be moved around, e.g., a worksite such as a vehicle, etc. Where one or more of the components to be mixed into the multi-component material has a relatively low viscosity (e.g., 100,000 centipoise or lower; 50,000 centipoise or lower; 25,000 centipoise or lower; etc.) it may be advantageous to incorporate valves into the dispensing system to reduce unwanted leakage of the component(s) with viscosities low enough to allow for leakage as the dispenser is manipulated into a variety of orientations during use. In connection with the present invention, valves may be incorporated in a number of locations within the system.

Figure 1E:
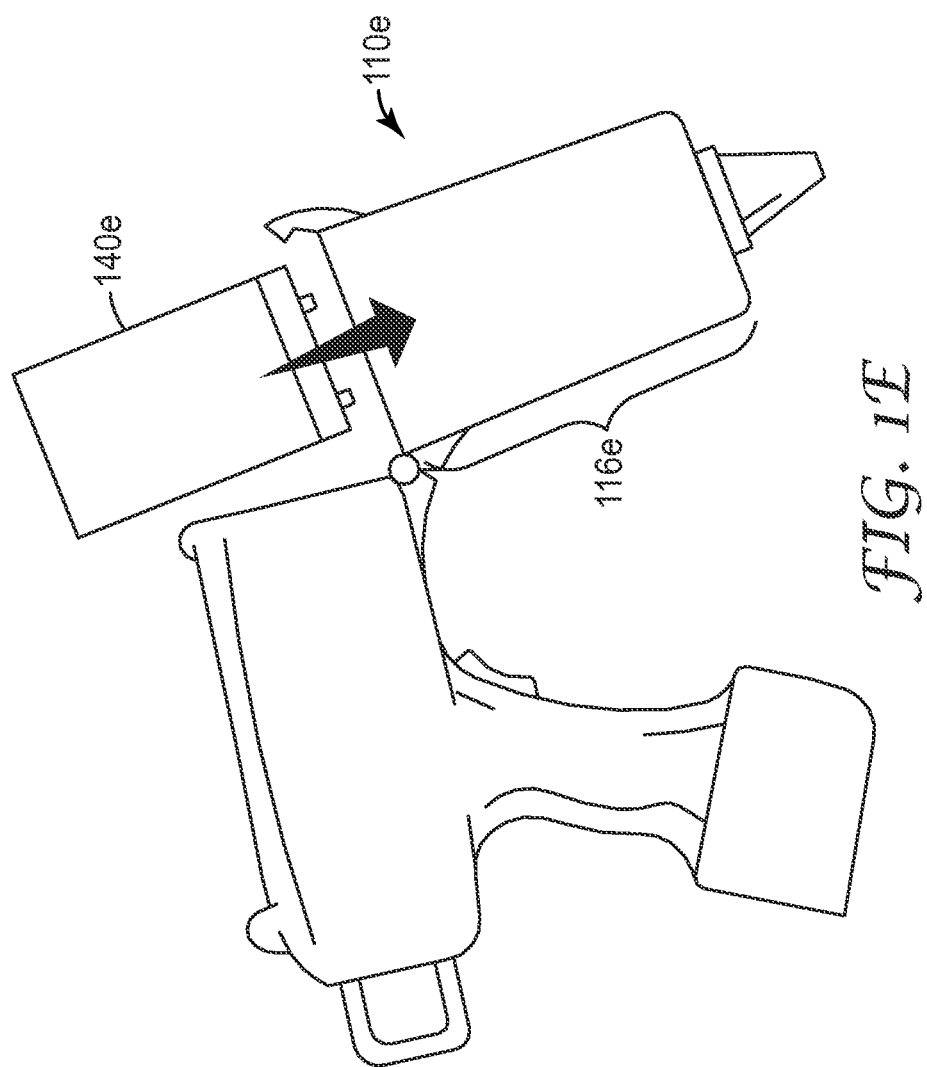
Figure 1G:
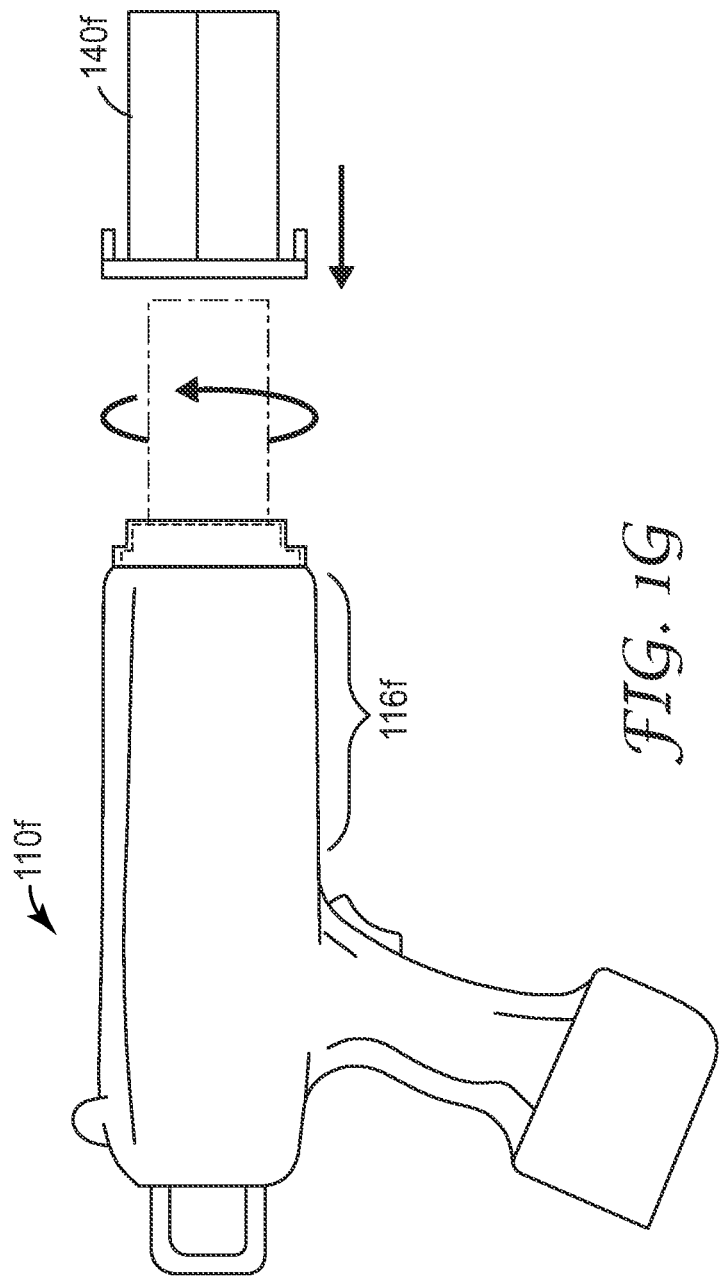

As discussed herein, it may be advantageous to provide the components to be mixed into the multi-component material in a cartridge-based system including a housing and containers in which the components are provided within the housing. Such cartridge-based systems may be loaded into a mobile dispenser in a variety of manners. FIG. 1D depicts one example in which a cartridge 140d is loaded into a top-loading compartment 116d of a dispenser 110d. FIG. 1E depicts another embodiment in which a cartridge 140e is loaded into a compartment 116e of a dispenser 110e that is hinged. FIG. 1F depicts another example in which a cartridge 140f is loaded into compartment 116f through the front of the dispenser 110f. FIG. 1G depicts yet another embodiment in which a cartridge 140f is loaded into compartment 116f using a twist-and-lock attachment mechanism which secures the cartridge 140f into place. The twist-and-lock attachment feature eliminates the need for the additional housing used in the embodiments depicted in FIGS. 1D-1F.

Figure 2A:
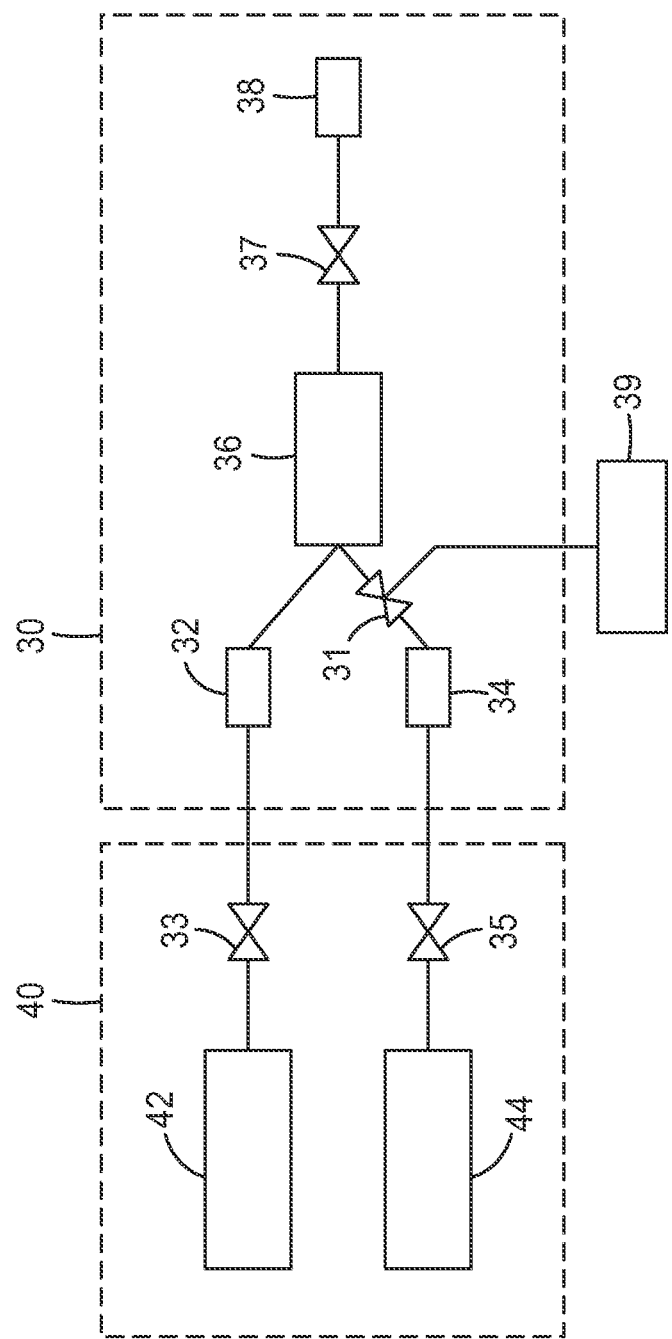
FIG. 2A is a block diagram of one exemplary flowpath for mixing and dispensing a multi-component material in accordance with the present invention.

FIG. 2A is a block diagram of one exemplary flowpath for mixing and dispensing a multi-component material in accordance with the present invention. Among the elements depicted in FIG. 2A are containers 42 and 44 in which the components to be mixed are located. The containers 42 and 44 are preferably connected to the mixing device 30 which includes an inlet 32 to receive the component stored in container 42 and an inlet 34 to receive the component stored in container 44. The mixing device 30 also includes a mixing chamber 36 in which the components received in the inlets 32 and 34 are mixed before passing to an outlet 38.

The flowpath depicted in FIG. 2A also includes an optional valve 33 located between the container 42 and the inlet 32, as well as an optional valve 35 located between the container 44 and the inlet 34. The valves 33 and 35 may preferably be supplied to prevent unwanted movement of the component carried in the containers into the mixing device 30. In some embodiments in which the mixing chamber 36 is purged, one or both of the valves 33 and 35 may also be one-way valves such that the material used to purge the mixing chamber 36 is prevented from (or substantially inhibited from) entering the containers 42 and 44 from which the components are provided.

The flowpath of FIG. 2A also includes an optional valve 37 located between the mixing chamber 36 and the outlet 38 of the mixing device 30. Valve 37 may preferably be supplied to prevent unwanted dispensing of the mixed multi-component material from the mixing chamber 36 out of the outlet 38 of the mixing device 30.

The valves 33, 35, and 37 depicted in FIG. 2A may all preferably be normally-closed and able to prevent the passage of materials therethrough when, for example, the container, cartridge and/or dispenser are oriented such that gravity acts on the materials being impeded by the valve. As such, unwanted leakage of the materials may be reduced or prevented during use of the dispensing systems of the present invention. It may further be preferred that the valves open in response to fluid pressure from the components in containers 42 and 44 in the case of valves 33 and 35 and from the mixed multi-component material in the mixing chamber 36 in the case of valve 37.

The valves used in connection with the present invention may preferably be described as pressure relief valves, that is, valves that open in response to an increase in pressure above a selected cracking pressure (the valves may also function as one-way or check valves). That cracking pressure may preferably be selected such that manipulation of the dispenser into a variety of orientations will not result in leakage unless an external force (supplied by, e.g., pistons, bladders, etc.) acts on the containers in which the components are located. The valves may take any suitable form, e.g., flapper valves, slit valves, ball valves, etc. Examples of some potentially suitable pressure relief valves may be found in, e.g., U.S. Patent Application Publication No. US 2006/0175434 (Escoto et al.), titled LIQUID SUPPLY ASSEMBLY, published on Aug. 10, 2006.

Figure 2B:
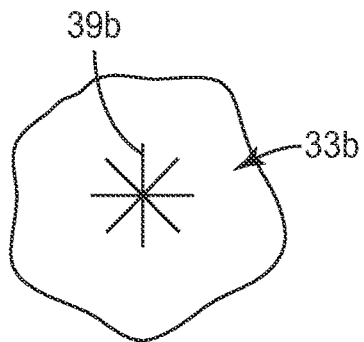
FIGS. 2B-2E depict exemplary embodiments of valve structures.
Figure 2C:
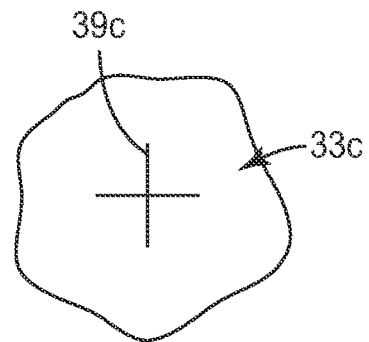
Figure 2D:
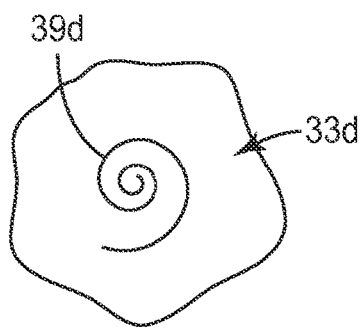
Figure 2E:
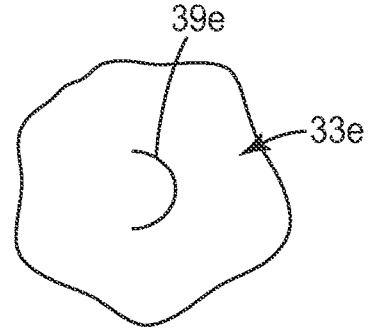

Examples of some potentially suitable valve designs are depicted in FIGS. 2B-2E. Each of the structures depicted in FIGS. 2B-2E may preferably be provided in the form of a sheet (or sheet-like structure) interposed across a flowpath, with one or more slits formed through the sheet such that pressure exerted on one side of the sheet causes the slit(s) to separate and open a path for the material to pass through the valve structure. The exemplary valve structure 33b depicted in FIG. 2B includes slits 39b formed through the body which can be a sheet-like layer of any suitable material or materials, e.g., spring steel, nylon, etc. The thickness of the sheets and the length and orientation of the slits may be selected to provide the desired cracking or opening pressure. The slits 39b in FIG. 2B are in the form of an asterisk pattern formed by four different slits that intersect at a central location. FIG. 2C depicts another exemplary valve design in which the valve structure 33c includes a pair of intersecting slits 39c. FIG. 2D depicts yet another exemplary embodiment in which the valve structure 33d includes a spiral slit 39d. FIG. 2E depicts still another embodiment of a valve structure 33e that includes a slit 39e in the form of a curved arc. Many other alternative valve designs are possible.

Yet another valve option may include a silicone valve placed in the outlet of a cartridge, with the valve opening being constrained by a sheet (formed of, e.g., nylon, metal, etc.) with an opening that is located over the valve, with the flat sheet fastened, welded, glued, or otherwise attached to over the silicone valve.

Referring again to FIG. 2A, the dispenser may also incorporate one or more dumping valves to control the ratio of the components mixed into the multi-component material. The flow diagram of FIG. 2A includes one such dumping valve 31 located between the inlet valve 34 and the mixing chamber 36, although a dumping valve may be located at any suitable point in the flowpath between the containers 42 and/or 44 and the mixing chamber 36. For example, dumping valves may be located between the outlet valves 33 and/or 35 and their respective inlets 32 and 34 into the mixing chamber 36. The dumping valve 31 is depicted as connected to a reservoir 39 that is adapted to contain any material redirected by the dumping valve 31. Such a reservoir 39 is, however, optional, and may or may not be included as a part of any system. The dumping valve 31 may be binary (i.e., open or closed) or it may be adjustable such that the amount of material shunted out of the flowpath (i.e., away from the mixing chamber 36) can be adjusted.

Figure 3:
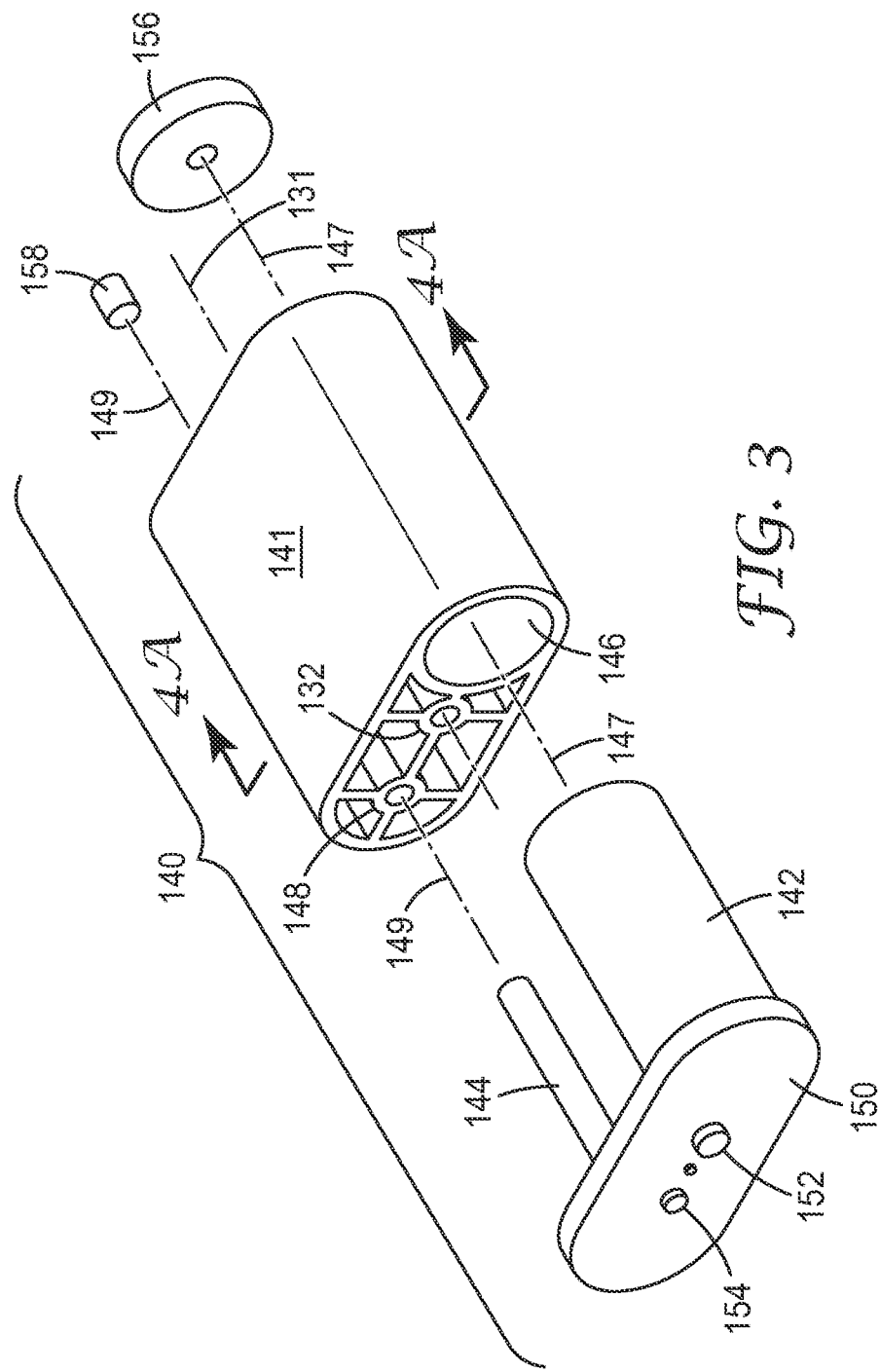
FIG. 3 is an exploded view of one exemplary cartridge that may be used in a mixing and dispensing apparatus of the present invention.
Figure 4A:
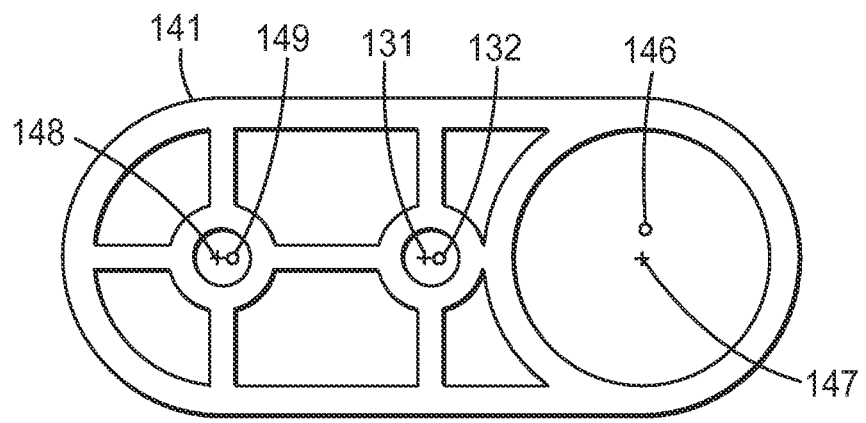
FIG. 4A is a cross-sectional view of the cartridge housing of the cartridge of FIG. 3, taken along line 4A-4A in FIG. 3.

One exemplary cartridge 140 that may be used in connection with the present invention is depicted in an exploded view in FIG. 3. The cartridge 140 of FIG. 3 includes a housing 141 that may preferably be sized and configured to fit within a dispenser in accordance with the present invention. FIG. 4A is a cross-sectional view of the cartridge housing 141 of the cartridge of FIG. 3, taken along line 4A-4A in FIG. 3. The depicted cartridge 140 includes a first container 142 and a second container 144. The first container 142 preferably contains a first component and the second container 144 preferably contains a second component, with the first and second components being mixed together as discussed herein to provide multi-component material including both the first component and the second component.

The first container 142 is preferably sized to fit within a first cavity 146 in the housing 141 and the second container 144 is preferably sized to fit within a second cavity 148 in the housing 141. It may be preferred that, as depicted, the cavities 146 and 148 in the housing 141 are in the form of right circular cylinders extending along axes 147 and 149 that are generally parallel to each other. Alternative arrangements for the cavities 146 and 148 are envisioned, such as, e.g., tubular cavities with non-circular cross-sectional shapes (e.g., oval, elliptical, semicircular, rectangular, triangular, etc.), cavities that extend along axes that are not generally parallel with each other, etc.

In some embodiments such as the depicted one, the cartridge housing 141 may also include a mixer drive passageway 132 extending through the housing 141. The mixer drive passageway 132 may be provided to accept a mixer drive shaft that passes through the cartridge 140 (such as mixer drive shaft 28 depicted in connection with FIG. 1). It may be preferred that the mixer drive passageway 132 extend along a drive axis 131 that, as in the depicted embodiment, is generally parallel to the either or both of the axes 147 and 149 extending through the first cavity 146 and the second cavity 148. In place of a mixer drive passageway, the housing 141 may incorporate a housing shaft that couples with a dynamic mixer on one end and a drive mechanism on the opposite end, such that the housing shaft is used to drive a dynamic mixer and a separate drive shaft need not be inserted through the housing 141 when loading a cartridge 140.

Another optional feature depicted in connection with the embodiment of FIG. 3 is a cap 150 to which both the first container 142 and the second container 144 are attached. It may be preferred that the cap 150 include the flow paths (not shown) that lead from the interiors of the containers 142 and 144 to the cartridge outlets 152 and 154 on the cap 150. The depicted cap 150 is a one-piece, completely integral article, although caps may be used in connection with the present invention that are composite structures (some examples of which are described herein). The cap 150 may preferably be attached to the housing 141 when the containers 142 and 144 are located within the cavities 146 and 148 in the housing 141.

Dispensing of the components in the containers 142 and 144 may preferably be accomplished by driving a piston through the cavities 146 and 148 from the end opposite the cap 150 (in which the cartridge outlets 152 and 154 are located). The containers 142 and 144 may preferably be collapsible, such that a piston driven through each cavity collapses the container to force the component contained therein out through the cartridge outlet in fluid communication with the collapsing container. Examples of some potentially suitable materials for collapsible containers may include, e.g., film/foil laminates, etc. such as those used in connection with dental impression/restorative materials. Other potentially suitable materials for collapsible containers may include, e.g., thin metal tubes, plastic containers, containers with accordion-shaped walls, etc.

The depicted cartridge 140 also includes optional pistons 156 and 158 sized to move through cavities 146 and 148 (respectively). The pistons 156 and 158 may be retained within the cavities 146 and 148 with a separate component acting on the pistons 156 and 158 to advance them through the cavities in which they are located. The pistons 156 and 158 may preferably extend over the entire cross-sectional area of the cavity in which they are located. In such an embodiment, the pistons 156 and 158 are located in the cavities 146 and 148 before the cartridge 140 is loaded into a dispenser. Alternatively, the pistons 156 and 158 may not be provided as a component of the cartridge 140, but may rather be inserted into the cavities 146 and 148 after the cartridge 140 is loaded into a dispenser. It may be preferred that the pistons 156 and 158 be constructed such that they can move in the both directions within the cavities 146 and 148 such that if a plunger reverse mechanism (see FIG. 1B and accompanying description) is provided to relieve residual pressure when the plungers are not actively driven.

The different cross-sectional areas of the two cavities 146 and 148 preferably correspond closely to the cross-sectional areas of the containers 142 and 146 inserted in them. Furthermore, the difference in the cross-sectional areas of the containers 142 and 146 preferably also corresponds to the volumetric ratio between the components to be mixed in a dispenser in which the cartridge 140 is used (assuming that plungers are advanced in each cavity at the same rate). In other words, if the volumetric ratio of the component in container 142 to the component in container 146 should be 50:1 in the mixed multi-component material, then the cross-sectional area of cavity 146 is preferably fifty times the cross-sectional area of cavity 148 (such that the ratio of the cross-sectional areas of the cavities is also 50:1).

Figure 4B:
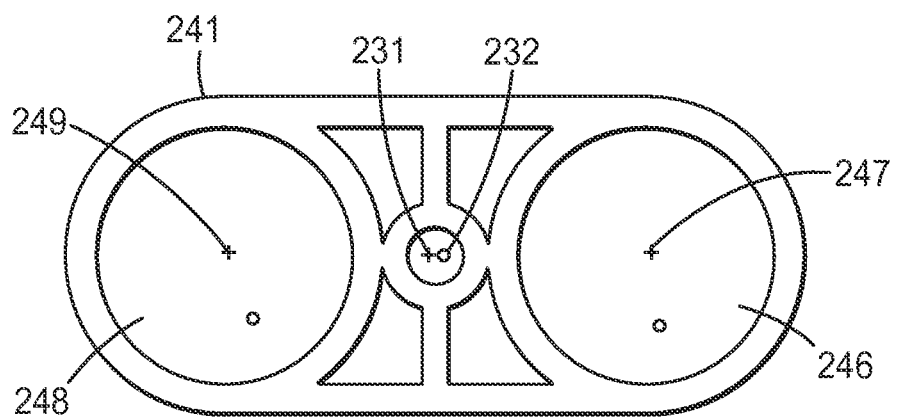
FIG. 4B is a cross-sectional view of a cartridge housing that is an alternative to the cartridge housing of FIGS. 3 & 4A.

FIG. 4B is a cross-sectional view of a cartridge housing 241 that is an alternative to the cartridge housing 141 of FIGS. 3 & 4A. In alternative housing 241, the first cavity 246 and the second cavity 248 are essentially equal. If correspondingly-sized containers were used in connection with the housing 241, the volumetric ratio of components delivered from containers in each of the cavities 246 and 248 would be 1:1 (assuming that plungers are advanced in each cavity at the same rate).

Among the features depicted in connection with the housing 241 are axis 247 which extends through cavity 246 and axis 249 which extends through cavity 248. As discussed in connection with housing 141 of cartridge 140, it may be preferred that the axes 247 and 249 of the cavities 246 and 248 be generally parallel to each other. Also depicted in FIG. 4B is an optional mixer drive passageway 230 that extends along axis 231. It may also be preferred that the drive passageway axis 231 be generally parallel to one or both of the cavity axes 247 and 249.

Another feature depicted in connection with the housings 141 and 241 of FIGS. 4A and 4B are the locations of the first cavities 146 and 246 relative to the second cavities 148 and 248. Because the different cartridges are capable of delivering components with different volumetric ratios, the different cartridges may preferably be used in connection with the same dispenser to mix and dispense different multi-component materials in which the components are supplied at different ratios. For example cartridge housing 141 can be used in a cartridge to supply components in a 50:1 volumetric ratio, while cartridge housing 241 can be used in a cartridge to supply components in a 1:1 volumetric ratio.

It may be preferred, as depicted in FIGS. 4A and 4B, that the axes along which the cavities in the two housing 141 and 241 are aligned be in the same positions within both housings 141 and 241 to allow substitution of cartridges into the same dispenser with minimal complications (such as, e.g., plunger alignment, etc.). In addition, the location of mixer drive passageways 130 and 230 in the two housings may also be consistent between the two housings 141 and 241.

The housings 141 and 241 of FIGS. 4A and 4B depict one approach in which the cross-sectional areas of cavities for containers carrying the components to be mixed into a multi-component material are different to provide different volumetric ratios. In another approach, the cross-sectional areas of one or more of the cavities within a housing may be reduced by providing a spacer in the cavity. One example of the use of spacer in a cavity is depicted in FIG. 5A, which is a cross-sectional view of another housing 341a with cavities 346a and 348a adapted to accept containers of different components as described herein.

Unlike the housings 141 and 241, however, the housing 341a includes a spacer 360a that reduces the open or unoccupied cross-sectional area of the second cavity 348a. The spacer 360a reduces the cross-sectional area of the second cavity 348a by a selected amount such that the open or unoccupied cross-sectional area 361a that remains in the cavity 348a is preferably less than the cross-sectional area of the second cavity 348a. The spacer 360a could occupy as little as, for example, 1% of the cross-sectional area of the second cavity 348a. In other exemplary embodiments, the spacer 360a could occupy 1% or more, 5% or more, or even 10% or more of the cross-sectional area of the second cavity 348a. In other embodiments, a spacer provided in a cavity of a cartridge housing of the present invention may occupy 25% or more of the cross-sectional area of the cavity (leaving 75% or less of the cross-sectional area of the cavity open for a container to be located therein). In still other embodiments, it may be preferred that the spacer occupy 50% or more of the cross-sectional area of the cavity (leaving 50% or less of the cross-sectional area of the cavity open for a container to be located therein). In still other embodiments, it may be preferred that the spacer occupy 75% or more, 90% or more, 95% or more, 98% or more, etc., of the cross-sectional area of the cavity (leaving the remaining volume/area to be occupied by a component container).

The spacers used in the cavities of the cartridges of the present invention may be provided as one-piece, integral articles inserted into a cavity to provide a smaller open volume within the cavity that can receive a container. Alternatively, the spacers may be provided in two or more pieces.

Figure 5A:
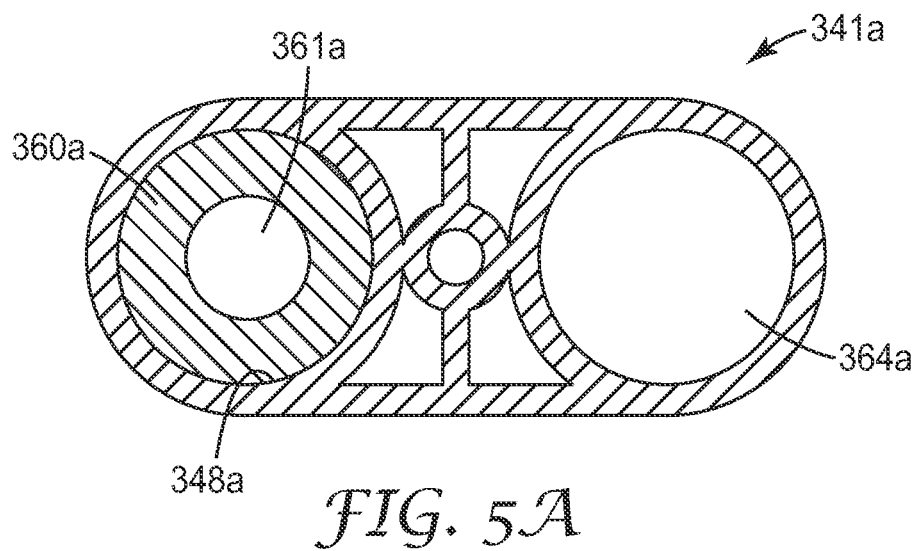
FIG. 5A is a cross-sectional view of another alternative cartridge housing including a spacer.

It may be preferred that the spacers used to provide a reduced open, unoccupied cross-sectional areas in cavities may form an open cross-sectional area (such as area 361a) that is centered within the cavity in which the spacer is located (as seen with spacer 360a in cavity 348a as depicted in FIG. 5A). This is not, however, required.

Figure 5B:
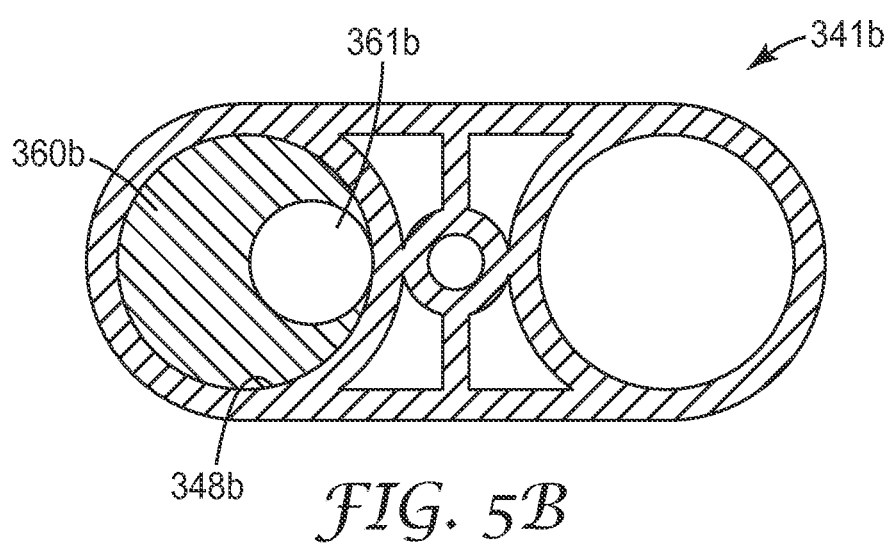
FIG. 5B is a cross-sectional view of another alternative cartridge housing including a different spacer.

FIG. 5B is a cross-sectional view of another spacer 360b located within a cavity 348b of a cartridge housing 341b. The spacer 360b defines an open, unoccupied cross-sectional area 361b within cavity 348b that is not centered within the cavity. Rather, the open cross-sectional area 361b is offset to one side and the spacer 360b itself has a generally crescent-shaped cross-section. It should be understood that spacers with many other shapes could be used in place of the two spacers 360a and 360b described herein.

Figure 5C:
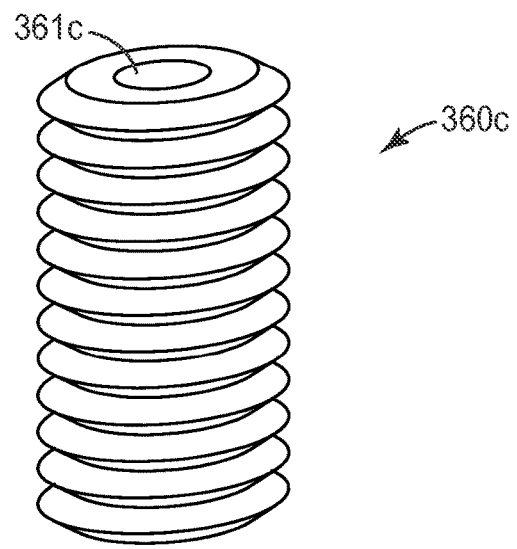
FIG. 5C is a perspective view of an alternative spacer that may be used in a cartridge in connection with the present invention.

Although the spacers used in cavities of cartridges according to the present invention may be substantially incompressible, FIG. 5C depicts another alternative spacer 360c in the form of a collapsible spacer designed to be compressed by a plunger moving through the cavity in which the spacer is located. The collapsible spacer 360c may include a series of accordion style folds or pleats as depicted in FIG. 5C or any other suitable compressible construction (e.g., compressible foams, etc.).

Although the spacer 360c is compressible along its length, it is preferred that the cross-sectional area of the open, unoccupied space 361c within the spacer 360c remain substantially unchanged as the spacer 360c is compressed along its length. The depicted accordion-style pleats are one construction for achieving that objective.

Figure 5D:
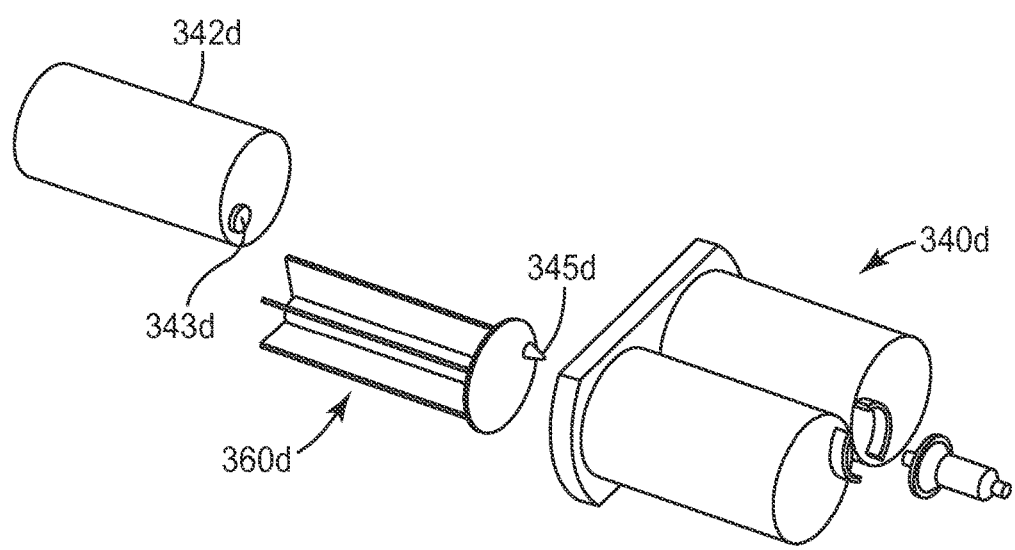
FIG. 5D is a perspective exploded view of another alternative cartridge housing with a spacer and a component container adapted for use with the spacer.
Figure 5E:
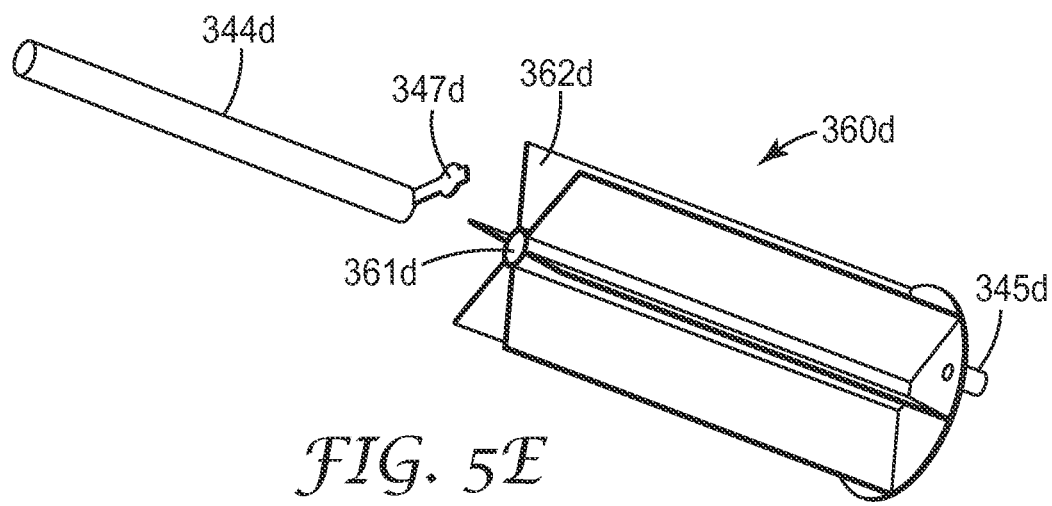
FIG. 5E is a perspective exploded view of the spacer and the component container of FIG. 5D.

Still another embodiment of a cartridge 340d and some of its various components is depicted in FIGS. 5D & 5E. The cartridge 340d includes a first container 342d and a spacer 360d in which a second container 344d is located (see FIG. 5E). The spacer 360d is used to position the second container 344d at a selected location within the cavity formed in the cartridge housing 341d. The spacer 360d includes central cavity 361d with radial struts 362d extending outwardly from the central cavity 361d to hold the central cavity 361d at the selected location.

The containers 342d and 344d each include an outlet 343d and 345d (respectively) through which materials exit from the containers 342d and 344d. In the depicted embodiment, those outlets are located off-center within the cavities provided in the housing 341d. Because, however, the spacer 360d retains the second container 344d in a location that is not aligned with the outlet 345d, the container 344d preferably includes a transverse channel 347d that provides a flowpath for material to travel from the body of the container 344d to the outlet 345d as seen in, e.g., FIG. 5E.

Although the transverse channel 347d is depicted as being a part of the second container 344d, in some embodiments the transverse channel 347d may be provided as a part of the spacer 360d, with the second container 344d mating with the spacer 360d and transverse channel 347d in a manner that allows materials forced out of the second container 344d to pass through the transverse channel 347d and into the outlet 345d.

Referring again to FIG. 3, the cartridges and elements depicted therein may be supplied as a unit such that the consumer would use the cartridge 140 to dispense and mix components contained in the cartridge and then dispose of the entire cartridge as a unit. Alternatively, various elements of the cartridges used in connection with the present invention may be re-used to reduce the cost and/or waste generated by use of the present invention.

In one embodiment, containers and the cap to which they are attached may be discarded after use, while the cartridge housing is reused. In some instances, the cartridge housing itself may be an integral part of the dispenser. In such a system, the containers holding the components to be mixed to form the multi-component material may be provided together or they may be provided separately, such that a user can selectively match different components to produce a multi-component material that has selected properties.

Other variations in the cartridges used in connection with the present invention may also be possible. For example, although the cartridges may include cavities that are arranged side-by-side as depicted in FIG. 3, it should be understood that some cartridges used in connection with the present invention may take a co-axial form such as that described in, e.g., U.S. Patent Application Publication No. US 2006/0151531 (Tikusis) titled APPARATUS AND METHODS FOR MIXING CAULK AND COLORANT; U.S. Patent Application Publication No. US 2006/054636 A1 (Brennan et al.) titled DUAL FLUID CARTRIDGE FOR STORING AND DISPENSING FLUIDS IN UNEQUAL RATIOS; and International Patent Publication No. WO 2005/095225 (Hermon et al.) titled DISPENSER FOR TWO COMPONENTS AND METHOD FOR DISPENSING FIRST AND SECOND COMPONENTS. Other coaxial cartridge designs may be used for supplying the different components to be mixed in the dispensers and methods of the invention.

Another variation is that the cartridge itself may incorporate a mixer drive shaft such that a drive element from the mixer drives a shaft resident in the cartridge. That resident shaft then connected to a mixing device that may be mounted on the cartridge itself or on the dispenser in which the cartridge is used.

Figure 6:
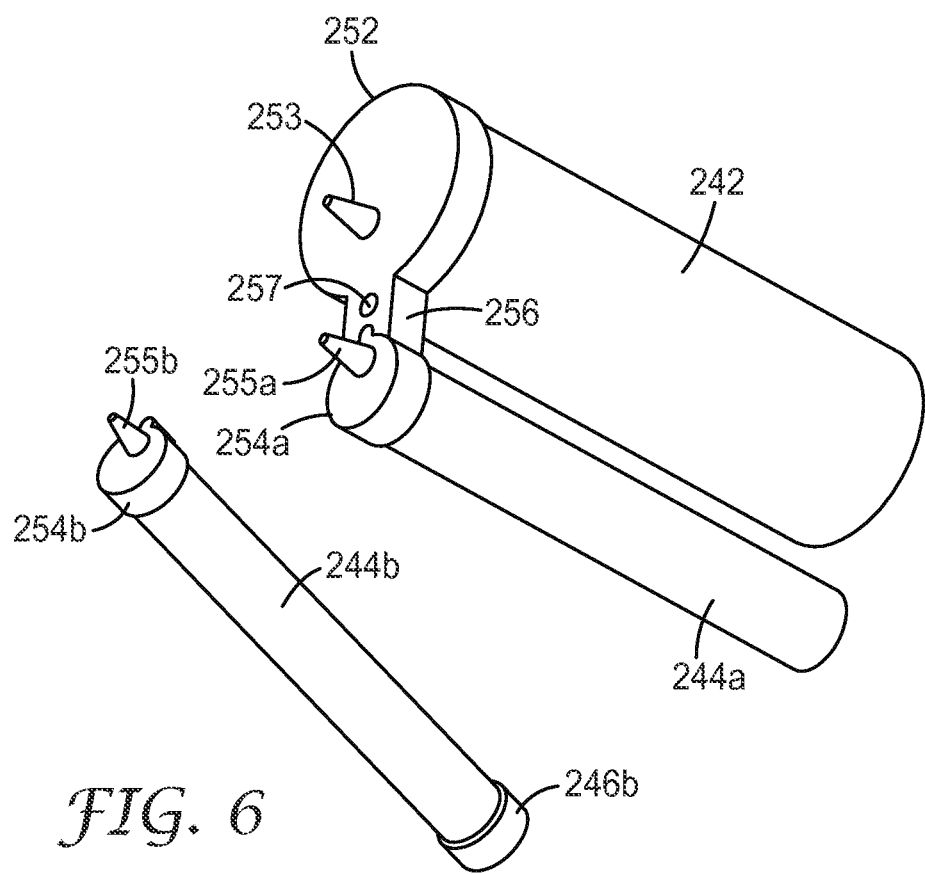
FIG. 6 is a perspective view of a two container insert that may be used in connection with a cartridge housing, along with an interchangeable second container.

FIG. 6 depicts one embodiment in which containers to be used in a cartridge housing may be paired up to provide multi-component material with selected characteristics. The containers 242 is attached a cap 252 while container 244a is attached to a cap 254a. Cap 252 may preferably include a nozzle 253 through which material exits from the container 242 as the container 242 is, e.g., collapsed as described herein. The cap 252 may also preferably include a valve (not shown) as described herein to provide control over the exit of material from the container 242.

The cap 254a may also preferably includes a nozzle 255a through which material exits from the container 244a as it is, e.g., collapsed as described herein. The cap 254a may also preferably include a valve (not shown) as described herein to provide control over the exit of material from the container 244a.

The caps 252 and 254a attached to the two containers may preferably include an interlocking mechanism such that the two caps can be attached together as depicted in FIG. 6. In the depicted embodiment, cap 252 includes an extension 256 to which cap 254a is attached. The extension 256 includes an optional bore 257 through which, e.g., a drive shaft for operating a dynamic mixer, may extend.

The system of FIG. 6 may also include an optional container 244b that may replace the container 244a attached to container 242. The container 244b may also preferably includes cap 254b. The cap 254b may preferably include a nozzle 255b through which material exits from the container 244b as the container is, e.g., collapsed as described herein. The cap 254b may also preferably include a valve (not shown) as described herein to provide control over the exit of material from the container 244b.

The different containers 244a and 244b may be used for a variety of reasons. In some embodiments (such as that depicted in FIG. 6), the containers 244a and 244b may be used to provide the same component in containers with different cross-sectional areas. When coupled with the same container 242, the different cross-sectional areas of the containers 244a and 244b can be used to provide different volumetric ratios of the two components, e.g., the container 244b with the smaller cross-sectional area can be used to provide a larger volumetric ratio between the component in container 242 as compared to the component in container 244b.

Another potential use for providing different containers 244a and 244b for use with the same container 242 may be to supply a different component for mixing with the component in container 242. For example, the different containers 244a and 244b may contain different hardeners (e.g., different peroxide hardeners) for use with a filler provided in container 242, they may contain two different colors, etc.

It may be preferred that, in the system of caps 252, 254a, and 254b, the nozzles 255a and 255b associated with each of the caps 254a and 254b are located in the same position with respect to nozzle 253 on cap 252 when the different caps are attached to each other (even though the attached containers 244a and 244b have different cross-sectional areas). This consistent spacing can be advantageous when the different caps and containers are used in a dispensing system.

Another optional feature depicted in connection with FIG. 6 is that container 244b includes an integral plunger cap 246b located on the end of the collapsible container 244b that is opposite the cap 254b. The integral plunger cap 246b is preferably constructed of rigid material and may be provided to interface with a plunger (such as, e.g., plungers 26 and 126 in FIGS. 1 & 1A) to distribute the applied force over the entire cross-sectional area of the container 244b. Although only container 244b is depicted with the optional plunger cap 246b, all of the containers used in connection with a dispenser or cartridge could be supplied with similar end caps.

The precise nature of the attachment between the collapsible containers of FIG. 6 and their associated caps may vary. In some embodiments, the containers may be formed of film/foil laminates that may be attached to the caps using thermal welding, sonic welding, chemical welding, mechanical fasteners (e.g., clamps, friction-fit rings, etc.); adhesives, adhesive tapes, spin welding, etc.

FIGS. 6A-6D depict some examples of potential techniques for attaching a container 242 to a cap 252 in connection with the present invention. In the depicted examples, the containers may preferably be in the form of a flexible material such as a film/foil laminate, polymer film, etc., although other materials may be used for the container.

Figure 6A:
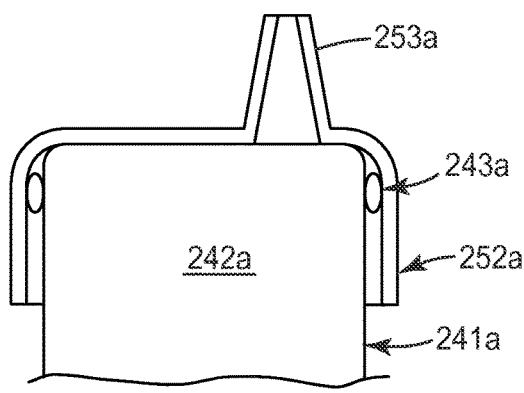
FIGS. 6A-6D depict various exemplary techniques for attaching a cap to a collapsible container.

The cap 252a of FIG. 6A includes a nozzle 253a and the wall 241a of the container 242a is preferably seated within the cap 252a. In the depicted embodiment, a seal is provided in the form of adhesive 243a located between the wall 241a and the interior of the cap 252a. The adhesive 243a may be in the form of, e.g., hot melt adhesive, pressure sensitive adhesive, curable adhesive (e.g., epoxy, etc.), or any other suitable material that is capable of retaining the wall 241a sealed within the cap 252a.

In use, an opening may preferably be formed in the wall 241a of the container 242a by any suitable technique, e.g., the wall 241a may be pierced, punctured, torn, burst, etc. such that component material within the container 242a can pass into the nozzle 253a without leaking or escaping between the seal created by the adhesive 243a between the container 242a and the cap 252a.

Figure 6B:
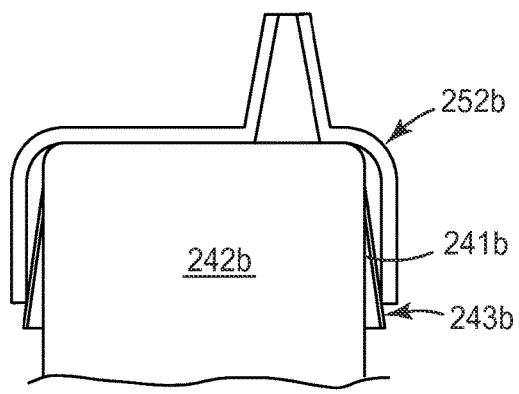

FIG. 6B depicts an alternative construction in which a container 242b is seated and sealed within cap 252b using a sleeve 243b. The sleeve 243b may be attached to the container 242b securely through, e.g., welding (chemical, thermal, ultrasonic, etc.) such that it is firmly attached to the wall 241b of the container 242b. The sleeve 243b is preferably capable of seating securely against the interior of the cap 252b such that as component material is dispensed under pressure from the container 242b, the sleeve 243b forms a leak-resistant seal with the interior of the cap 252b. The sleeve 243b may preferably be formed of any suitable material that provides the desired flexibility to deform and seal against the interior of the cap 252b as well as provide a firm attachment to the container wall 241b (e.g., polyethylenes, polyurethanes, etc.). In some instances, the sleeve 243b may include a structure that mates with complementary structure in the interior of the cap 252b to enhance sealing performance.

As another alternative, the sleeve 243b may be attached to the cap 252b (by, e.g., molding the sleeve with the cap, etc.). In such a construction, the sleeve 243b may or may not be flexible—especially if the container wall 241b is flexible enough to create an adequate seal as material within the container 242b is pressurized during dispensing.

Figure 6C:
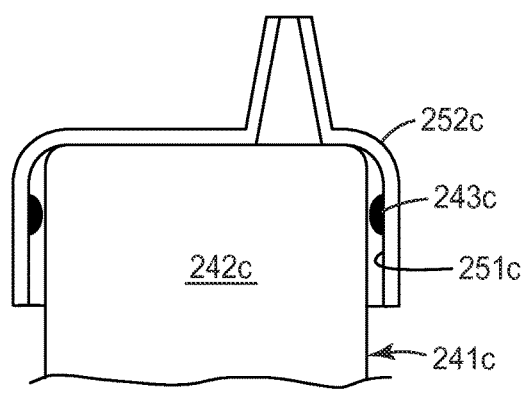

FIG. 6C depicts another alternative for providing a seal between a container 242c and cap 252c. In the depicted embodiment, an O-ring 243c is attached to the interior 251c of the cap 252c to provide a seal with the exterior of the wall 241c of the container 242c. The O-ring 243c may be attached to the interior 251c of the cap 252c by any suitable technique, e.g., adhesives, insert molding, flanges, etc. The container 242c itself may also be attached to the interior 251c of the cap 252c (in addition to the O-ring 243c) using, e.g., adhesive or some other technique—with the O-ring 243c providing a seal between the wall 241c and the interior 251c of the cap 252c.

Figure 6D:
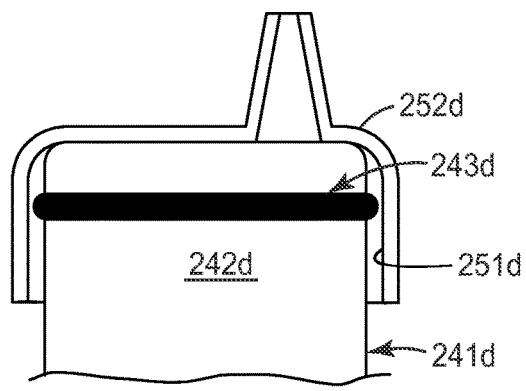

FIG. 6D presents yet another exemplary attachment technique in which container 242d is attached to the interior of the cap 252d. In the embodiment of FIG. 6D, an O-ring 243d is attached to the wall 241d of the container 242d, such that as the container 242d is pressurized during the dispensing operation, the wall 241d and attached O-ring 243d will be forced against the interior 251d of the cap 252d to provide a leak-resistant seal. As with the embodiment depicted in FIG. 6C, the container 242d itself may also be attached to the interior 251d of the cap 252d using, e.g., adhesive or some other technique—with the O-ring 243d providing a seal between the wall 241d and the interior 251d of the cap 252d.

As discussed herein, the systems of the present invention include a mixing device such as, for example, mixing device 30 on dispenser 10. The mixing device may take the form of a static mixer or a dynamic mixer. Examples of some potentially suitable dynamic mixers that may be used in connection with the present invention may include dynamic mixers described in U.S. Pat. No. 5,249,862 (Herold et al.); U.S. Pat. No. 6,394,643 (Bublewitz et al.); U.S. Pat. No.

6,837,399 (Wagner et al.); U.S. Pat. No. 6,932,243 (Keller); etc. Other potentially suitable dynamic mixers may be described in, e.g., U.S. Patent Application Publication Nos. US 2003/0137898 (Wagner et al.); US 2004/0085854 (Pauser et al.); etc. Examples of some potentially suitable static mixers may include those described in U.S. Pat. No. 4,093,188 (Horner); U.S. Pat. No. 4,801,008 (Rich); U.S. Pat. No. 5,413,253 (Simmen); and U.S. Pat. No. 5,609,271 (Keller et al.).

In some embodiments, the mixing device may be attached to the cap or caps that are attached to the containers carrying the components to be mixed. In such an embodiment, the mixing device and the cap may be provided as integral parts of a unitary structure. In other embodiments, the mixing device may be provided as an independent element that is attached to the cap of the cartridge or container cap. In still other systems, the mixing device may be attached to a dispenser in which the containers/cartridges are located.

Figure 7:
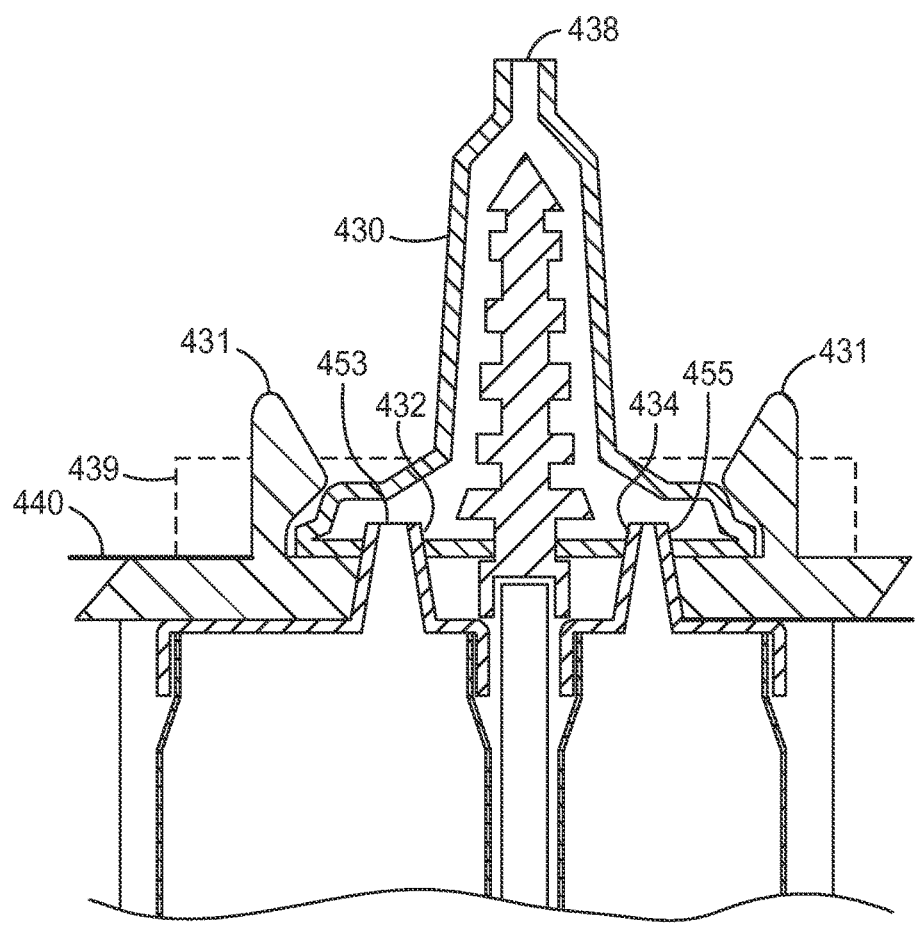
FIG. 7 is a cross-sectional view of one exemplary mixing device and technique for attaching the mixing device to a housing.

In the embodiments in which the mixing device is provided as an independent element (whether attached to the cartridge itself or a dispenser in which the cartridge is used), it may be attached by a variety of techniques. The attachment may include threaded elements, snap-on attachments, external collars that retain the mixing device in place, snap tabs, etc. One example of a potentially suitable attachment technique is depicted in FIG. 7 in which a mixing device 430 is attached to cartridge 440 by a pair of tabs 431 extend over the edges of the base of the mixing device 430. The tabs 431 preferably resiliently move outward as the mixing device 430 is seated such that the nozzles 453 and 455 from the cartridge 440 are seated in the inlets 432 and 434 of the mixing device 430. A collar 439 is depicted in broken lines in FIG. 7 and may be used in addition to the tabs 431 to assist in retaining the mixing device 430 in place. The collar 439 may be retained in place by any suitable technique, e.g., threads, snap-fit mechanisms, etc.

Figure 7A:
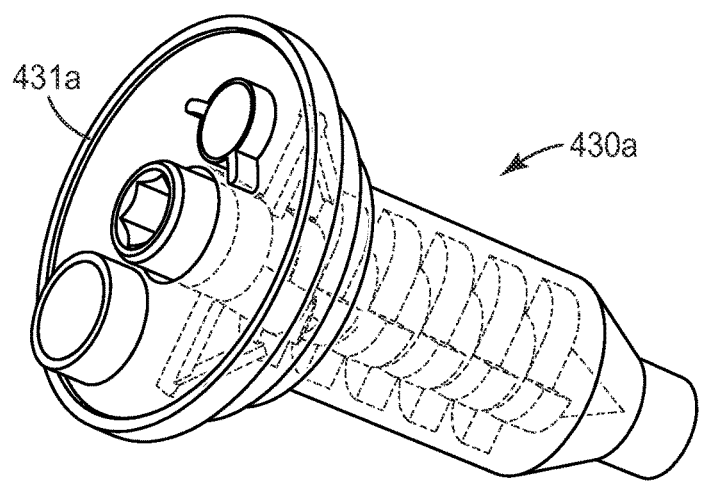
FIG. 7A is a perspective view of another exemplary mixing device attachment structure.

Although FIG. 7 depicts one technique for attaching a mixing device to either a dispenser or cartridge, alternatives attachment techniques may be used. One example is depicted in FIG. 7A in which the mixing device 430a is, itself, provided with tabs 431a that extend from the mixing device 430a. The tabs will preferably mate with complementary slots or openings on a dispenser or cartridge such that the mixing device 430a is retained in place during operation of the dispenser. The spacing, shape, and/or size of the tabs 431a may be used to assist in proper alignment of the mixing device on a dispenser/cartridge—on other words, the tabs 431a may need to be properly aligned with complementary slots/openings to allow for attachment of the mixing device 430a.

Figure 7B:
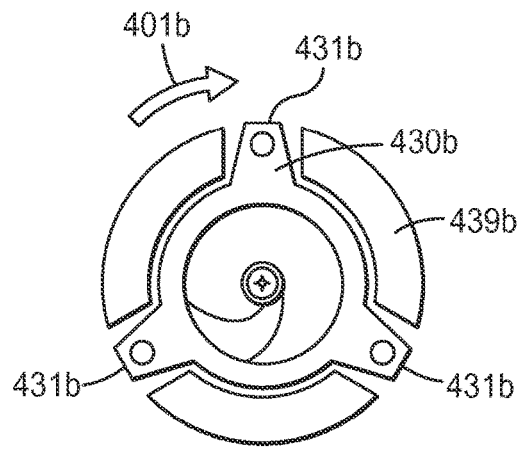
FIGS. 7B-7E depict examples of alternative mechanisms for retaining a mixing device in position.

FIGS. 7B-7E depict additional alternative techniques for attaching mixing devices to a cartridge or dispenser. In FIG. 7B, the mixing device 430b includes three arms 431b that extend outwardly from the mixing device 430b. The arms 431b preferably cooperate with flanges 439b to retain the mixing device 430b in position as the mixing device 430b is rotated in the direction indicated by arrow 401b. For example, the arms 431b may preferably fit within slots formed by flanges 439b. As an alternative, to rotating the mixing device 430b, it may be possible to rotate flanges 439b in the direction of arrow 401b while the arms 431b of the mixing device 430b remain stationary.

Figure 7C:
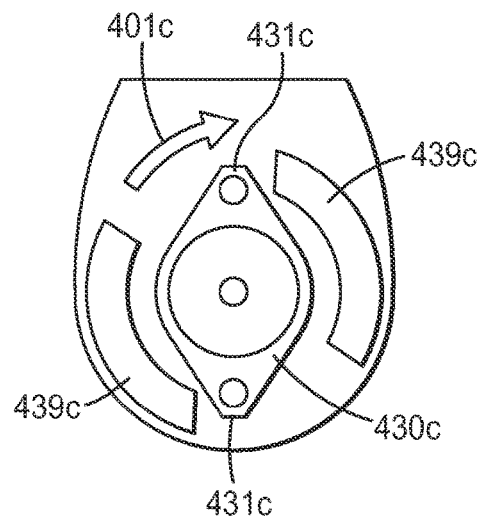

The mechanism depicted in FIG. 7C includes two arms 431c that extend outwardly from the mixing device 430c. The arms 431c preferably cooperate with flanges 439c to retain the mixing device 430c in position as the mixing device 430c is rotated in the direction indicated by arrow 401c. For example, the arms 431c may preferably fit within slots formed by flanges 439c. As an alternative, to rotating the mixing device 430c, it may be possible to rotate flanges 439c in the direction of arrow 401c while the arms 431c of the mixing device 430c remain stationary.

Figure 7D:
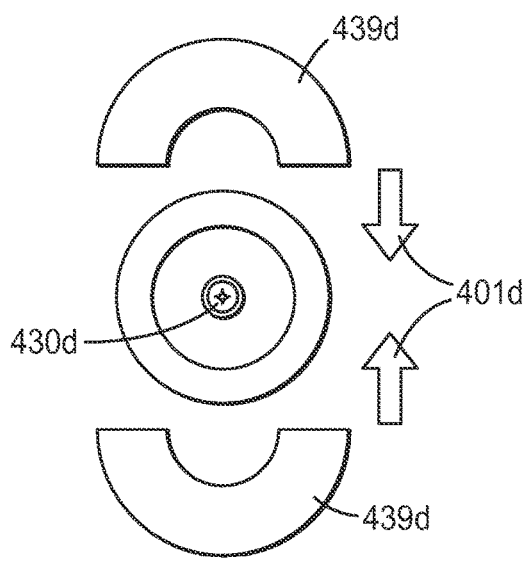

Still another retention mechanism is depicted in FIG. 7D. The mixing device 430d in FIG. 7D is retained in position by a pair of flanges 439d that move towards each other in the directions indicated by arrows 401d to retain the mixing device 430d in place. Although FIG. 7D indicated that both flanges 439d move, in some embodiments it may be possible that only one of the flanges 439d moves while the opposing flange 439d remains stationary.

Figure 7E:
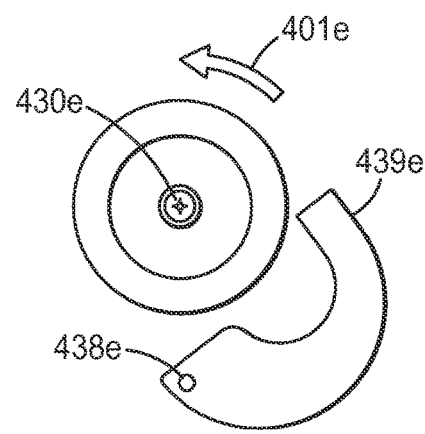

FIG. 7E depicts yet another retention mechanism for retaining mixing device 430e. The mechanism includes a flange 439e that rotates about point 438e in the direction of arrow 401e to move into position to retain the mixing device 430e in a selected position.

Figure 7F:
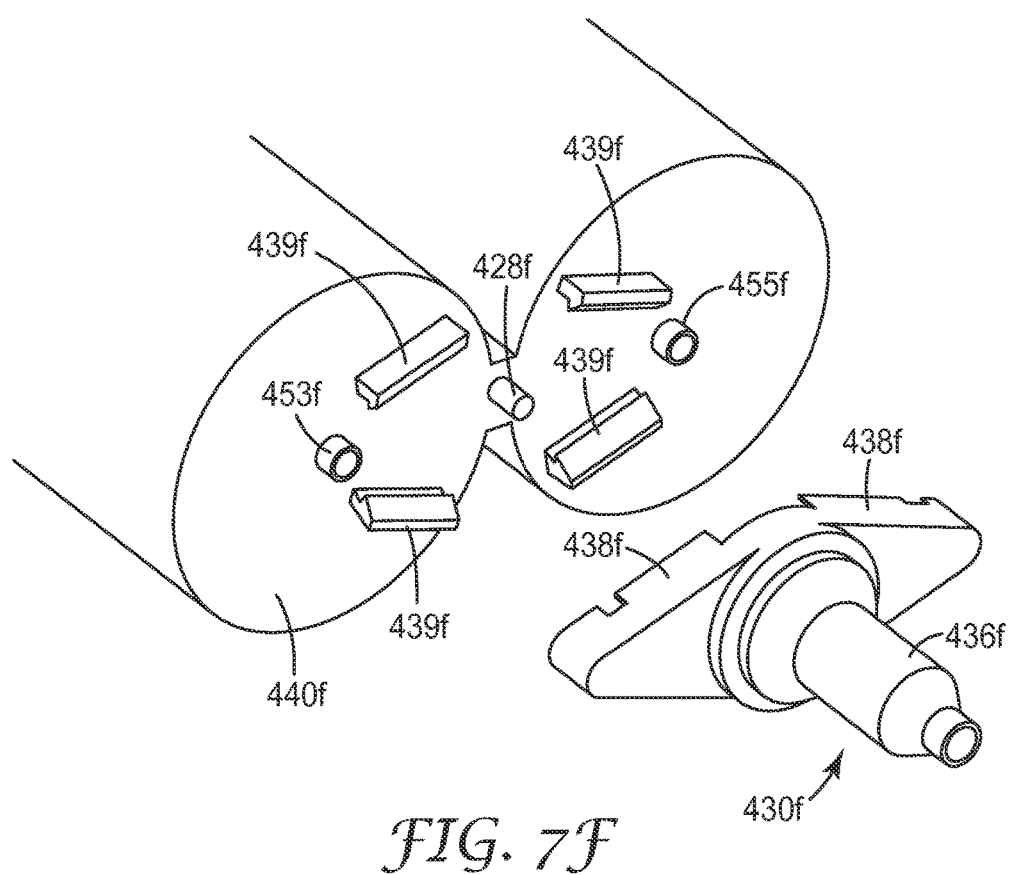
FIG. 7F is a perspective exploded view of another mixer device and attachment structure for retaining the mixer device.

FIG. 7F depicts another mixing device 430f and an alternative retention mechanism for retaining the mixing device 430f on either a cartridge or a dispenser in which cartridges can be loaded. The depicted mixing device 430f includes a base 438f that spans the distance between the outlets 453f and 455f through which the components are delivered to the mixing device 430f.

Because the mixing device 430f includes a mixing chamber 436f that is centrally located between the outlets 453f and 455f, the mixing device 430f may preferably include channels (not shown) that deliver the components to the mixing chamber 436f. It may be preferred that the channels form leakproof seals with the outlets 453f and 455f such that the components exiting the outlets are delivered to the mixing chamber 436f.

In addition the system depicted in FIG. 7F includes an optional drive shaft 428f that protrudes from the surface 440f such that the drive shaft 428f can mate with a driven element in the mixing device 430f if the mixing device 430f is a dynamic mixer as discussed herein. Although the drive shaft 428f and complementary mixing chamber 436f of the mixing device 430f are depicted as being centered between the outlets 453f and 455f, in some embodiments, the various features may not be centered.

The retention mechanism depicted in FIG. 7F includes tabs 439f that extend from the surface 440f. The mixing device 430f is, itself, also provided with structures 438f that preferably mate with the tabs 439f on the surface 440f such that the mixing device 430f is retained in place during operation. The spacing, shape, and/or size of the tabs 439f and associated structures on the mixing device 430f may be used to assist in proper alignment of the mixing device on a dispenser/cartridge—in other words, the tabs 439f may need to be properly aligned with complementary structures on the mixing device 430f to allow for attachment and retention of the mixing device 430f.

In some embodiments in which a drive shaft is included in the cartridge and/or device, it may be advantageous if the drive shaft is retractable to assist in removal and/or attachment of a mixing device. One embodiment of a retractable drive shaft is depicted in connection with a cartridge assembly 570 in FIG. 8. The depicted cartridge assembly 570 includes a cartridge 540 adapted to be received and retained within a compartment 516 that may be permanently or removably attached to a dispenser (not shown). The cartridge 540 may preferably include containers that hold components to be mixed into multi-component material.

The compartment 516 includes a retractable drive shaft 528 that passes through a passageway (not shown) in the compartment 516. The terminal end 527 of the drive shaft 528 preferably protrudes from the terminal end 517 of the compartment 516 in its normal or unbiased position. In the depicted embodiment, the terminal end 527 of the drive shaft 528 can, however, be displaced from its unbiased position such that the terminal end 527 of the drive shaft 528 can be partially or completely retracted into the compartment 516 such that a smaller portion or none of the terminal end 527 of the drive shaft 528 protrudes from the compartment 516. Retraction of the terminal end 527 of the drive shaft 528 may facilitate removal and/or replacement of a mixing device (not shown).

Figure 8:
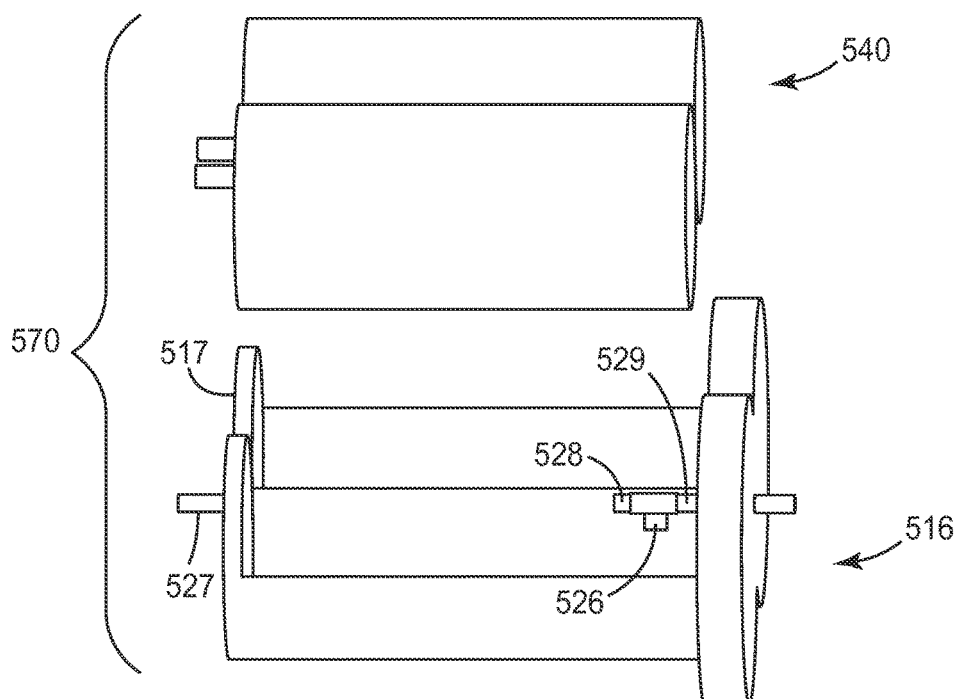
FIG. 8 is a perspective exploded view of another embodiment of a cartridge assembly including a retractable mixer drive shaft.
Figure 9:
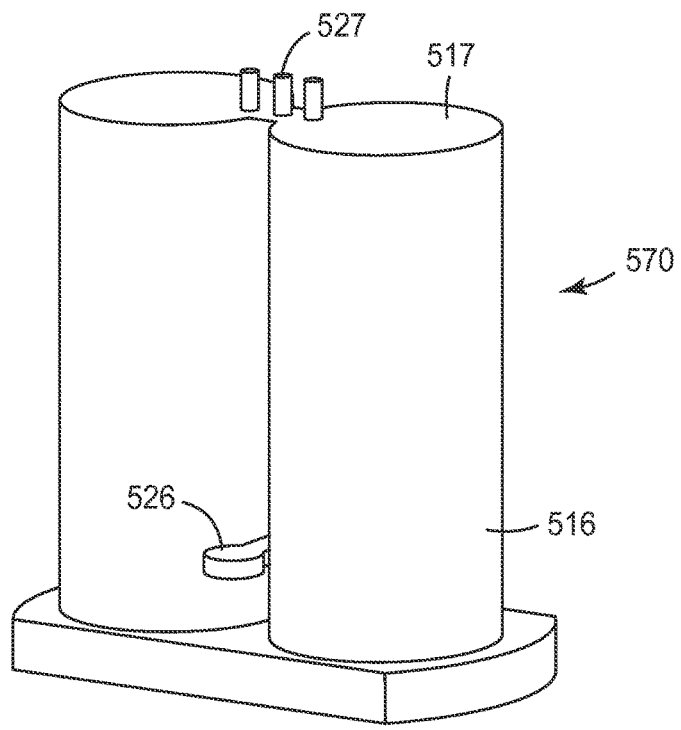
FIG. 9 is a perspective view of the opposite side of the compartment in the cartridge assembly of FIG. 8.

The drive shaft 528 may be biased (forced) into its unbiased position by one or more resilient members. In the depicted embodiment, the drive shaft 528 is held in its unbiased position (with the terminal end 527 protruding from the compartment 516) by a coil spring 529. When the coil spring 529 is in its extended position, the terminal end 527 of the drive shaft 528 protrudes from the compartment 516 as seen in FIG. 8. Compression of the spring 529 is, in the depicted embodiment, preferably caused by using a lever 526 that protrudes from the compartment 516 as seen in FIG. 9. Forcing the lever downward (in the view of FIG. 9) preferably compresses the spring 529 and retracts the terminal end 527 of the drive shaft 528 into the compartment (partially or completely).

Although the depicted structure can be used to provide a retractable drive shaft, many other mechanisms could also be used or substituted for those found in the depicted embodiment. For example, the coil spring could be replaced by any suitable resilient member such as an elastomeric member, leaf spring, etc.

Figure 10A:
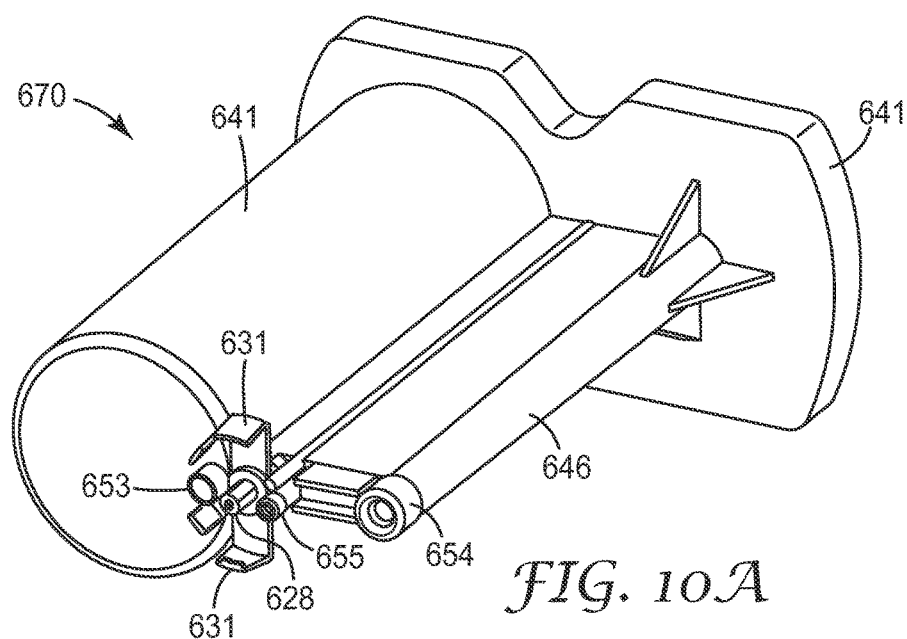
FIGS. 10A & 10B depict another exemplary cartridge assembly that may be used in connection with the present invention.
Figure 10B:
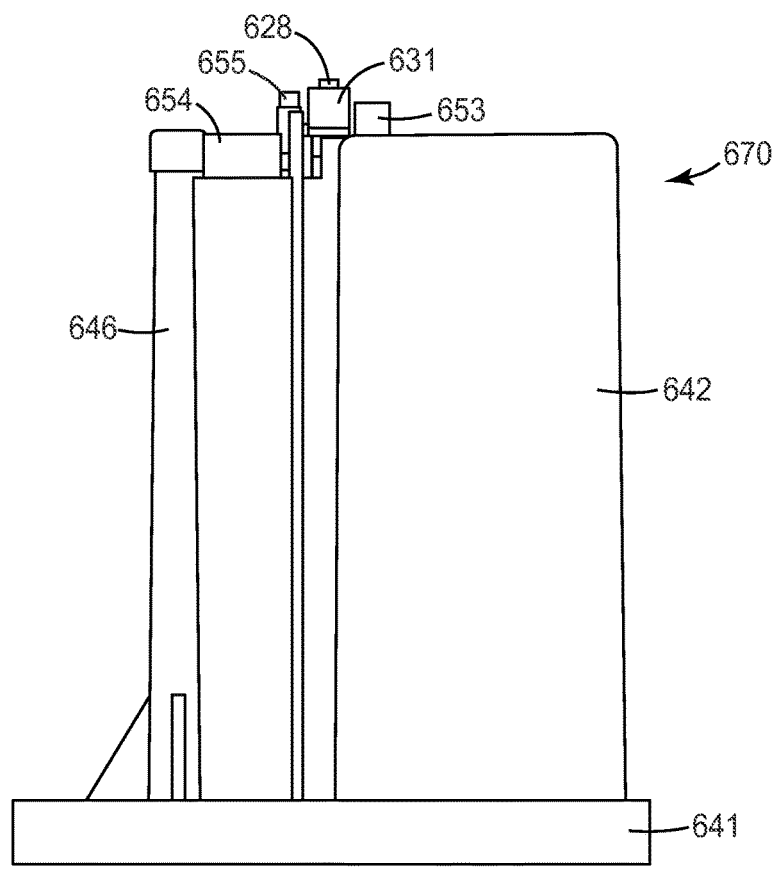

Still another embodiment of a cartridge assembly 670 that may be used in connection with the present invention is depicted in FIGS. 10A & 10B. The cartridge assembly 670 includes a first container 642 and a second container 646 attached to a base 641. The first container 642 and the second container 646 extend from a base 641 towards a dispensing end located distal from the base 641.

A mixing device (not shown) may be attached to the cartridge assembly 670 using tabs 631. A mixer drive shaft 628 preferably is provided to drive the mixing device if needed.

The first container 642 delivers materials to a mixing device through outlet 653 and the second container 646 delivers materials to the mixing device through outlet 655. The cartridge assembly 670 includes a channel 654 used to deliver material to the outlet 655 from the second container 646 because the container 646 is, itself, located outside of the outlet 655.

One potential advantage of the cartridge assembly 670 is that its base 641 provides a flat surface such that the cartridge assembly 670 can stand upright on table, or other flat surface, horizontal surface. The ability to stand upright can make use and storage of the cartridge assembly 670 more convenient. If a drive shaft 628 is provided in the cartridge assembly 670, it may be preferred that the drive shaft 628 does not protrude past the base 641 such that the cartridge assembly 670 can stand on the base 641 on a flat horizontal surface.

Figure 11A:
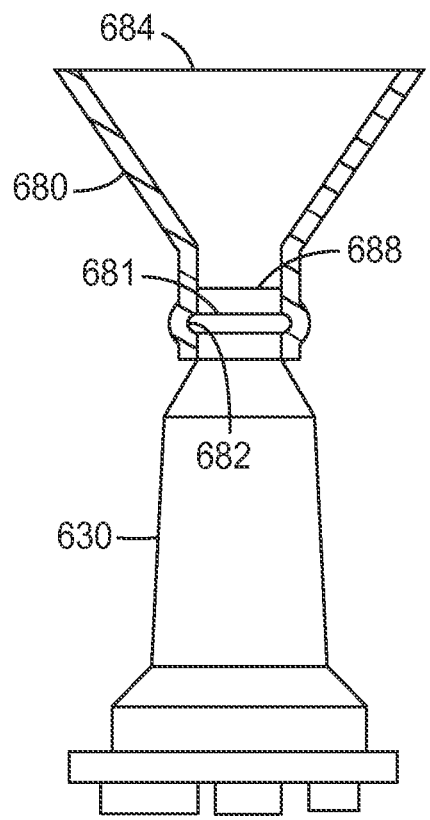
FIG. 11A depicts one exemplary flow shaping attachment on the outlet of a mixing device.

Another feature that may be included in connection with the present invention is that the outlet 438 (see FIG. 7) of the mixing device 430 may be fitted with a variety of attachments to provide a selected shape for the multi-component material exiting the mixing device. FIG. 11A depicts one embodiment of a mixing device 630 with a flow shaping attachment 680 attached to the outlet 638 of the mixing device 630.

The flow shaping attachment 680 is retained on the outlet 638 in the depicted embodiment by a raised ridge 681 that fits within a channel 682 in the flow shaping attachment 680. Many alternative techniques for retaining the flow shaping attachment 680 in place over the outlet 638 may be used, e.g., threaded components, collars, bayonet mounts, adhesives, etc.

Figure 11B:
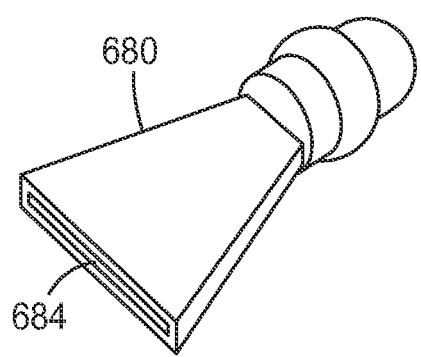
FIG. 11B is a perspective view of the flow shaping attachment of FIG. 11A.

The flow shaping attachment 680 depicted in FIG. 11A may preferably spread the flow of multi-component material exiting the outlet 684 such that it has a flattened, ribbon-like shape. A perspective view of the flow shaping attachment 680 is depicted in FIG. 11B, with the flow shaping attachment 680 including an outlet 684. In some instances, the width of the outlet 684 can be reduced by, e.g., removing a portion of the flow shaping attachment 680 to reduce the distance between the outlet 684 in the flow shaping attachment 680 and the outlet 638 to which the flow shaping attachment 680 is attached.

Figure 12A:
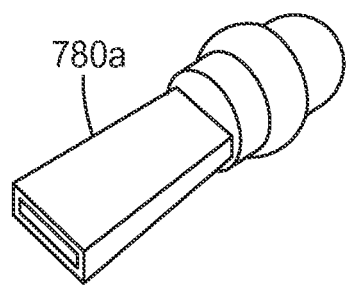
FIGS. 12A and 12B depict alternative flow shaping attachments that may be used to deliver multi-component material in a selected flow shape or profile.
Figure 12B:
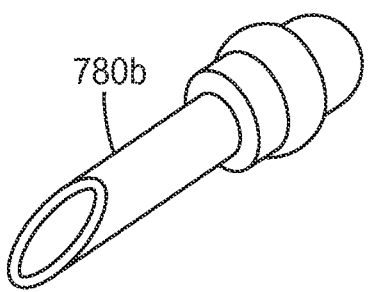

FIGS. 12A and 12B depict some exemplary alternative flow shaping attachments 780a and 780b, each of which includes a differently shaped flow shaping attachment that may be used in connection with the present invention. Other potential alternative flow-shaping attachments that may be used in connection with the present invention may be described in U.S. Pat. No. 6,520,702 (Heusser) titled ADAPTOR FOR A STATIC MIXER, as well as in U.S. Patent Application Publication No. US 2005/0127119 A1 (Keller) titled APPLICATOR FOR A DISPENSING APPLIANCE.

As discussed herein, the systems of the present invention may include one or more valves to control flow of material. In that regard, it should be noted that the flow shaping attachments themselves may include self-closing valves—either in addition to valves located elsewhere within the flowpath, or in place of valves located elsewhere in the flowpath.

Although the flow shaping attachments in FIGS. 11A, 11B, 12A, & 12B are depicted as independent articles that can be attached to the outlet of the mixing device, it should be understood that in some embodiments, the flow shaping attachments may be formed integrally with the mixing device (in which case no attachment mechanisms would be required).

Viscosity Measurements:

For those instances in which viscosity of the components to be mixed into the multi-component material are relevant, i.e., those situations in which actual viscosity is determined or in which viscosity ratios are relevant, the viscosity of the components may be determined using the procedures described in the Brookfield Digital Rheometer Model DV-III Operation Instruction Manual No. M/91-201-I297 (Brookfield Engineering Labs, Inc., Stoughton, Mass.). The spindle chosen and the shear rate selected for the test is dependent on the anticipated viscosity range. For higher viscosity materials (e.g., materials with a viscosity of 50,000 centipoise to 10,000,000 centipoise—such as some of the body filler components used in connection with the present invention), the Helipath T-bar spindles are used with the spindle selected such that the torque range falls between 10% to 100% at rotational speeds of 0.5 revolutions per minute to 20 revolutions per minute on the apparatus. For some exemplary body filler components used in connection with the present invention, the viscosity values are reported at 5 revolutions per minute using a T-C spindle. Lower viscosity materials (e.g., materials with a viscosity of 50,000 centipoise or less—such as some of the hardeners that may be used in connection with the present invention), the HA/HB spindle series is used to obtain viscosity measurements. All viscosity values obtained are at room temperature, i.e., at approximately 20 degrees Centigrade.

As used herein and in the appended claims, the singular forms "a," "and," and "the" include plural referents unless the context clearly dictates otherwise. Thus, for example, reference to "a spacer" includes a plurality of spacers (unless otherwise expressly indicated) and equivalents thereof known to those skilled in the art.

Unless otherwise indicated, all numbers expressing quantities of ingredients, viscosities, etc., in the specification and claims are to be understood as being modified by the term "about" in all instances. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

The complete disclosure of the patents, patent documents, and publications cited in the Background, the Detailed Description of Exemplary Embodiments, and elsewhere herein are incorporated by reference in their entirety as if each were individually incorporated.

Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A replaceable cartridge apparatus for use in a mobile dispenser, wherein the mobile dispenser includes a drive mechanism, the cartridge apparatus comprising:
a cartridge housing releasably attachable to the mobile dispenser, the cartridge housing comprising a first cavity located within the cartridge housing and a second cavity located within the cartridge housing, wherein the first cavity and the second cavity extend from a base end of the cartridge housing towards a dispensing end of the cartridge housing distal from the base end;
a first container located within the first cavity, the first container containing a first component of a curable multi-component material;
a second container located within the second cavity, the second container containing a second component of the curable multi-component material;
a mixer drive passageway extending through the cartridge housing and defining a drive axis; and
a rotatable drive shaft located within the mixer drive passageway, the drive shaft being adapted for releasable coupling to a dynamic mixer at the dispensing end while being adapted for releasable coupling to the drive mechanism of the mobile dispenser at the base end.

2. A cartridge apparatus according to claim 1, wherein the base end is flat and wherein the drive shaft does not protrude past the base such that the cartridge housing can stand on the base on a flat horizontal surface.

3. A cartridge apparatus according to claim 1, wherein the mixer drive passageway is located between the first cavity and the second cavity.

4. A cartridge apparatus according to claim 1, wherein the curable multi-component material comprises curable body repair material.

5. A cartridge apparatus according to claim 1, wherein the cartridge housing further comprises means for attaching the dynamic mixer to a delivery end of the housing, wherein the drive axis extends through the means for attaching.

6. A replaceable cartridge for use in a mobile dispenser, the cartridge apparatus comprising:
a cartridge housing releasably attachable to the mobile dispenser, the cartridge housing comprising a first cavity located within the cartridge housing, the first cavity comprising a first cross-sectional area transverse to a first axis that extends along a length of the first cavity, wherein the cartridge housing further comprises a second cavity located within the cartridge housing, the second cavity comprising a second cross-sectional area transverse to a second axis that extends along a length of the second cavity;
a spacer sized to fit within the second cavity of the cartridge housing, wherein the spacer extends along the length of the second cavity parallel to the second axis and defines a spacer cross-sectional area that occupies 1% or more of the second cross-sectional area, and wherein the spacer reduces an open cross-sectional area along the second axis within the second cavity;
a first container located within the first cavity, the first container containing a first component of a curable multi-component material; and
a second container located within the open cross-sectional area of the of the second cavity, the second container containing a second component of the curable multi-component material.

7. A cartridge according to claim 6, wherein the first cross-sectional area and the second cross-sectional area are substantially equal.

8. A cartridge according to claim 6, wherein the spacer cross-sectional area comprises 25% or more of the second cross-sectional area.

9. A cartridge according to claim 6, wherein the spacer cross-sectional area comprises 50% or more of the second cross-sectional area.

10. A cartridge according to claim 6, wherein the spacer comprises a rigid sleeve.

11. A cartridge according to claim 6, wherein the spacer comprises a compressible sleeve capable of compressing to a compressed length along the second axis that is 25% or less of an uncompressed length of the compressible sleeve.

12. A cartridge according to claim 6, wherein the curable multi-component material comprises curable body repair material.

13. A cartridge according to claim 6, wherein the first axis and the second axis are generally parallel to each other.

14. A cartridge according to claim 6, wherein the cartridge housing further comprises a mixer drive passageway located between the first cavity and the second cavity, the mixer drive passageway defining a drive axis that is generally parallel to the first axis and the second axis.

15. A cartridge according to claim 14, wherein the cartridge housing further comprises means for attaching a dynamic mixer to a delivery end of the housing, wherein the drive axis extends through the means for attaching.

16. A cartridge according to claim 1, further comprising a cap attachable to the cartridge housing and having first and second nozzles at the dispensing end of the cartridge housing and a bore through which the rotatable drive shaft extends, wherein the first and second containers form a fluid-tight seal with the cap and wherein the first and second components can exit through their respective nozzles.

17. A cartridge according to claim 6, wherein the open cross-sectional area is centered within the cavity in which the spacer is located.

* * * * *

UNITED STATES PATENT AND TRADEMARK OFFICE
CERTIFICATE OF CORRECTION

| | | |
|---|---|---|
| PATENT NO. | : 9,731,258 B2 | |
| APPLICATION NO. | : 11/957296 | |
| DATED | : August 15, 2017 | |
| INVENTOR(S) | : Jeffrey Janssen | |

It is certified that error appears in the above-identified patent and that said Letters Patent is hereby corrected as shown below:

On the Title Page

Column 2 (Other Publications), Line 2, delete "www.conprotec.com/" and insert -- www.comprotec.com/ --.

Page 2, Column 2 (Other Publications), Line 2, delete "Versuchsergenbnisse" and insert -- Versuchsergebnisse --.

In the Specification

Column 10, Lines 4-5, delete "of the of the" and insert -- of the --.

Column 13, Line 43, delete "of the of the" and insert -- of the --.

Column 20, Line 64, delete "10b," and insert -- 110b, --.

In the Claims

Column 38, Line 42, In Claim 6, delete "of the of the" and insert -- of the --.

Signed and Sealed this
Sixteenth Day of January, 2018

Joseph Matal
*Performing the Functions and Duties of the*
*Under Secretary of Commerce for Intellectual Property and*
*Director of the United States Patent and Trademark Office*